(12) United States Patent
Nie et al.

(10) Patent No.: US 12,202,894 B2
(45) Date of Patent: Jan. 21, 2025

(54) ANTI-TIM-3 ANTIBODIES

(71) Applicant: Wuxi Biologics Ireland Limited, Dublin (IE)

(72) Inventors: Siwei Nie, Shanghai (CN); Yong Zheng, Shanghai (CN); Jing Li, Shanghai (CN)

(73) Assignee: WuXi Biologics Ireland Limited, Dublin (IE)

( * ) Notice: Subject to any disclaimer, the term of this patent is extended or adjusted under 35 U.S.C. 154(b) by 1033 days.

(21) Appl. No.: 16/981,367

(22) PCT Filed: Mar. 19, 2019

(86) PCT No.: PCT/CN2019/078661
§ 371 (c)(1),
(2) Date: Sep. 16, 2020

(87) PCT Pub. No.: WO2019/179420
PCT Pub. Date: Sep. 26, 2019

(65) Prior Publication Data
US 2021/0163590 A1    Jun. 3, 2021

(30) Foreign Application Priority Data

Mar. 20, 2018 (WO) ............... PCT/CN2018/079624

(51) Int. Cl.
| | |
|---|---|
| *C07K 16/00* | (2006.01) |
| *A61K 39/395* | (2006.01) |
| *A61K 39/40* | (2006.01) |
| *C07H 21/04* | (2006.01) |
| *C07K 16/28* | (2006.01) |
| *C12N 1/20* | (2006.01) |
| *C12N 5/00* | (2006.01) |
| *C12P 21/04* | (2006.01) |
| *C12P 21/06* | (2006.01) |
| *C12P 21/08* | (2006.01) |
| *G01N 33/68* | (2006.01) |

(52) U.S. Cl.
CPC ..... *C07K 16/2803* (2013.01); *G01N 33/6893* (2013.01); *C07K 2317/24* (2013.01); *C07K 2317/52* (2013.01); *C07K 2317/565* (2013.01); *C07K 2317/732* (2013.01); *C07K 2317/734* (2013.01); *C07K 2317/92* (2013.01); *G01N 2333/70503* (2013.01)

(58) Field of Classification Search
None
See application file for complete search history.

(56) References Cited

U.S. PATENT DOCUMENTS

| | | |
|---|---|---|
| 4,560,655 A | 12/1985 | Baker |
| 4,657,866 A | 4/1987 | Kumar et al. |
| 4,767,704 A | 8/1988 | Cleveland et al. |
| 4,927,762 A | 5/1990 | Darfler |
| 5,122,469 A | 6/1992 | Mather et al. |
| 5,571,894 A | 11/1996 | Wels et al. |
| 5,587,458 A | 12/1996 | King et al. |
| 5,624,821 A | 4/1997 | Winter et al. |
| 5,648,260 A | 7/1997 | Winter et al. |
| 5,731,168 A | 3/1998 | Carter et al. |
| 6,005,079 A | 12/1999 | Casterman et al. |
| 6,248,516 B1 | 6/2001 | Winter et al. |
| 7,662,379 B2 * | 2/2010 | Presta .................. C07K 16/244 530/387.3 |
| 9,605,070 B2 | 3/2017 | Sabatos-Peyton et al. |
| 2012/0189617 A1 | 7/2012 | Takayanagi et al. |
| 2015/0218274 A1 | 8/2015 | Sabatos-Peyton et al. |
| 2016/0200815 A1 | 7/2016 | Feldman et al. |
| 2017/0088616 A1 | 3/2017 | Takayanagi et al. |
| 2017/0190777 A1 | 7/2017 | Sabatos-Peyton et al. |

FOREIGN PATENT DOCUMENTS

| | | |
|---|---|---|
| CN | 103079644 A | 5/2013 |
| EP | 0183070 | 6/1986 |
| EP | 0244234 | 11/1987 |
| EP | 0402226 | 12/1990 |
| EP | 0404097 | 12/1990 |
| TW | 201736397 A | 10/2017 |
| WO | WO 1987/000195 | 1/1987 |
| WO | WO 1990/003430 | 4/1990 |
| WO | WO 1993/011161 | 6/1993 |
| WO | WO 1993/016185 | 8/1993 |
| WO | WO 1994/004678 | 3/1994 |
| WO | WO 1994/025591 | 11/1994 |
| WO | WO 1994/029351 | 12/1994 |
| WO | WO 1999/051642 | 10/1999 |
| WO | WO 2006/034488 | 3/2006 |
| WO | WO-2013/006490 A2 | 1/2013 |
| WO | WO-2013/006490 A3 | 1/2013 |
| WO | WO-2016/068802 A1 | 5/2016 |

(Continued)

OTHER PUBLICATIONS

Dondelinger et al. Frontiers in Immunology. 2018, 9;2278:1-15. (Year: 2018).*

(Continued)

*Primary Examiner* — Chun W Dahle
(74) *Attorney, Agent, or Firm* — Fish & Richardson P.C.

(57) ABSTRACT

The present disclosure provides anti-TIM-3 antibodies or antigen-binding fragments thereof, isolated polynucleotides encoding the same, pharmaceutical compositions comprising the same, and the uses thereof.

23 Claims, 12 Drawing Sheets

Specification includes a Sequence Listing.

(56) References Cited

FOREIGN PATENT DOCUMENTS

| WO | WO-2016/071448 A1 | 5/2016 |
|---|---|---|
| WO | WO-2017/031242 A1 | 2/2017 |
| WO | WO-2017/178493 A1 | 10/2017 |
| WO | WO-2017/205721 A1 | 11/2017 |
| WO | WO-2018/013818 A2 | 1/2018 |
| WO | WO-2018/013818 A3 | 1/2018 |
| WO | WO-2018/036561 A1 | 3/2018 |

OTHER PUBLICATIONS

Dixon et al. Nature. Jul. 2021, 595:101-106. (Year: 2021).*
Sauer et al. Cancer Immunology, Immunotherapy 2023, 72:3405-3425. (Year: 2023).*
Ngiow, S.F. et al. (2011). "Prospects for TIM3-targeted antitumor immunotherapy," Cancer Res. 71:6567-6571.
Extended European Search Report mailed on May 3, 2021, for European Patent Application No. 19 772 139.2, 12 pages.
Kikushige, Y. et al.(2013), "TIM-3 as a novel therapeutic target for eradicating acute myelogenous leukemia stem cells," International Journal of Hematology 98:627-633.
Al-Lazikani et al., "Standard Conformations for the Canonical Structures of Immunoglobulins," Journal of Molecular Biology, 1997, 273(4):927-948.
Altschul et al., "Basic Local Alignment Search Tool," Journal of Molecular Biology, Oct. 5, 1990, 215(3):403-410.
Altschul et al., "Gapped BLAST and PSI-BLAST: a new generation of protein database search programs," Nucleic Acids Research, Sep. 1, 1997, 25(17):3389-3402.
Antibody Engineering, vol. 1, 2nd ed., 2010, Chapter 27, 411-430.
Barnes et al., "Methods for growth of cultured cells in serum-free medium," Analytical Biochemistry, Mar. 1, 1980, 102(2):255-270.
Batzer et al., "Enhanced evolutionary PCR using oligonucleotides with inosine at the 3'-terminus," Nucleic Acid Research, Sep. 25, 1991, 19(18):5081.
Brennan et al., "Preparation of bispecific antibodies by chemical recombination of monoclonal immunoglobulin G1 fragments," Science, Jul. 5, 1985, 229(4708):81-83.
Carter et al., "High level *Escherichia coli* expression and production of a bivalent humanized antibody fragment," Biotechnology, Feb. 1992, 10(2): 163-167.
Carter et al., "Humanization of an anti-p185HER2 antibody for human cancer therapy," Proceedings of the Natural Academy of Sciences, USA, May 15, 1992, 89(10):4285-4289.
Chothia et al., "Canonical structures for the hypervariable regions of immunoglobulins," Journal of Molecular Biology., Aug. 20, 1987, 196(4):901-917.
Chothia et al., "Conformations of immunoglobulin hypervariable regions," Nature, Dec. 21-28, 1989, 342(6252):877-883.
Chothia et al., "Domain association in immunoglobulin molecules The packing of variable domains," Journal of Molecular Biology Dec. 5, 1985, 186(3):651-663.
Chu et al., "Inhibition of B cell receptor-mediated activation of primary human B cells by coengagement of CD19 and FcgammaRIIb with Fc-engineered antibodies," Molecular Immunology, Sep. 2008, 45(15):3926-3933.
Cunningham et al., "High-resolution epitope mapping of hGH-receptor interactions by alanine-scanning mutagenesis," Science Magazine, Jun. 2, 1989, 244(4908):1081-1085.
Duncan et al., "The binding site for C1q on IgG," Nature, Apr. 21, 1988, 322(6166):738-740.
Ferris et al., "Too much of a good thing? Tim-3 and TCR signaling in T cell exhaustion," The Journal of Immunology, Aug. 15, 2014, 193(4):1525-1530.
GenBank Accession No. AAL65156.1 "T cell immunoglobulin mucin-3 [Mus musculus]" Feb. 11, 2002, 2 pages.
GenBank Accession No. AAL65158.1 "T cell immunoglobulin mucin-3 [*Homo sapiens*]" Feb. 11, 2002, 2 pages.
GenBank Accession No. CAD79372.1, "T cell immunoglobulin mucin-3, partial [Rattus norvegicus]," Jul. 26, 2016, 2 pages.
GenBank Accession No. EHH54703.1 "hypothetical protein EGM_15593 [Macaca fascicularis]" Mar. 17, 2015, 2 pages.
Graham et al., "Characteristics of a Human Cell Transformed by DNA from Human Adenovirus Type 5," Journal General Virology, 1977, 36:59-74.
Guss et al., "Structure of the IgG-binding regions of streptococcal protein G," EMBO J, Jul. 1986, 5:1567-1575.
Ham et al., "Media and growth requirements," Methods in Enzymology, 1979, 58:44-93.
Hamers-Casterman et al., "Naturally occurring antibodies devoid of light chains," Nature, Jun. 3, 1993, 363(6428):446-448.
Hansen et al., "Clathrin and HA2 adaptors: effects of potassium depletion, hypertonic medium, and cytosol acidification.," Journal of Cellular Biology, Apr. 1993, 121(1):61-72.
Hastings et al., "TIM-3 is expressed on activated human CD4+ T cells and regulates Th1 and Th17 cytokines," European Journal of Immunology, Sep. 2009, 39(9):2492-2501.
Higgins et al., "Using CLUSTAL for multiple sequence alignments," Methods in Enzymology, 1996, 266:383-402.
Hinton et al., "An engineered human IgG1 antibody with longer serum half-life," The Journal of Immunology, Jan. 1, 2006, 176(1):346-356.
Holliger et al., "Diabodies": small bivalent and bispecific antibody fragments, Proceedings of the Natural Academy of Sciences, USA, Jul. 15, 1993, 90(14):6444-6448.
Huston et al., "Protein engineering of antibody binding sites: recovery of specific activity in an anti-digoxin single-chain Fv analogue produced in *Escherichia coli*.," Proceedings of the Natural Academy of Sciences, USA, Aug. 1, 1988, 85:5879-5883.
Idusogie et al., "Engineered antibodies with increased activity to recruit complement," The Journal of Immunology., Feb. 15, 2001, 166(4):2571-2575.
Idusogie et al., "Mapping of the C1q binding site on rituxan, a chimeric antibody with a human IgG1 Fc," The Journal of Immunology., Apr. 15, 2000, 164(8):4178-4184.
International Preliminary Report on Patentability in Appln. No. PCT/CN2019/078661, mailed on Oct. 1, 2020, 7 pages.
International Search Report and Written Opinion in Appln. No. PCT/CN2019/078661, mailed on Jun. 24, 2019, 12 pages.
Jones et al., "Replacing the complementarity-determining regions in a human antibody with those from a mouse," Nature, 1986, 321(6069):522-525.
Koch-Nolte et al., "Single domain antibodies from llama effectively and specifically block T cell ecto-ADP-ribosyltransferase ART2.2 in vivo," The FASEB Journal, Nov. 2007, Jun. 15, 2007, 21(13):3490-3498.
Larkin et al., "Clustal W and Clustal X version 2.0," Bioinformatics (Oxford, England), Nov. 1, 2007, 23(21): 2947-2948.
Lazar et al., "Engineered antibody Fc variants with enhanced effector function," PNAS, Mar. 14, 2006, 103(11): 4005-4010.
Lefranc et al., "IMGT unique numbering for immunoglobulin and T cell receptor variable domains and Ig superfamily V-like domains," Developmental and Comparative Immunology, Jan. 2003, 27(1): 55-77.
Lefranc, "IMGT, the international ImMunoGeneTics information system: a standardized approach for immunogenetics and immunoinformatics," Immunome Research, 2005, 1(3), 11 pages.
Lindmark et al., "Binding of immunoglobulins to protein A and immunoglobulin levels in mammalian sera," The Journal of Immunology Meth., Aug. 12, 1983, 62(1):1-13.
Mather et al., "Culture of testicular cells in hormone-supplemented serum-free medium," Annals NY. Acad. Sci., 1982, 383:44-68.
Mather, "Establishment and characterization of two distinct mouse testicular epithelial cell lines," Biology of Reproduction, Aug. 1980, 23(1):243-252.
Molecular Biology of B Cell, 2nd ed., Oct. 9, 2014, Chapter 26, 481-514.
Morimoto et al., "Single-step purification of F(ab')2 fragments of mouse monoclonal antibodies (immunoglobulins G1) by hydropho-

(56) References Cited

OTHER PUBLICATIONS bic interaction high performance liquid chromatography using TSKgel Phenyl-5PW," Journal of Biochemical and Biophysical Methods, Mar. 1992, 24(1-2):107-117.

Muyldermans, "Single domain camel antibodies: current status," Reviews in Molecular Biotechnology, Jun. 2001, 74(4):277-302.

Nguyen et al. "Heavy-chain antibodies in Camelidae; a case of evolutionary innovation," Immunogenetics, Apr. 2002, 54(1):39-47.

Nguyen et al., "Heavy-chain only antibodies derived from dromedary are secreted and displayed by mouse B cells," Immunology, May 2003, 109(1):93-101.

Office Action in European Appln. No. 19772139.2, mailed on Jun. 6, 2023, 4 pages.

Oganesyan et al., "Structural characterization of a human Fc fragment engineered for lack of effector functions," Acta Crystallogrica Section D Biological Crystallography, Jun. 2008, 64(6):700-704.

Ohtsuka et al., "An alternative approach to deoxyoligonucleotides as hybridization probes by insertion of deoxyinosine at ambiguous codon positions," Journal of Biological Chemistry, Mar. 10, 1985, 260(5):2605-2608.

Presta et al., "Humanization of an antibody directed against IgE," Journal of Immunology, Sep. 1, 1993, 151(5):2623-2632.

Richards et al., "Optimization of antibody binding to FcgammaRIIa enhances macrophage phagocytosis of tumor cells," Molecular Cancer Therapeutics, Aug. 2008, 7(8):2517-2527.

Riechmann et al., "Reshaping human antibodies for therapy," Nature, Mar. 24, 1988, 332(6162):323-327.

Riechmann et al., "Single domain antibodies: comparison of camel VH and camelised human VH domains," Journal of Immunological Methods, Dec. 10, 1999, 231(1-2):25-38.

Rossolini et al., "Use of deoxyinosine-containing primers vs degenerate primers for polymerase chain reaction based on ambiguous sequence information," Molecular and Cellular Probes., Apr. 1994, 8(2):91-98.

Ryan et al., "Antibody targeting of B-cell maturation antigen on malignant plasma cells," Molecular Cancer Therapeutics, Nov. 2007, 6(11):3009-3018.

Sabatos-Peyton CA, et al., "Blockade of Tim-3 binding to phosphatidylserine and CEACAM1 is a shared feature of anti-Tim-3 antibodies that have functional efficacy," Oncoimmunology, Nov. 9, 2017, 7(2):e1385690, 10 pages.

Schier et al., "Isolation of Picomolar Affinity Anti-c-erbB-2 Single-chain Fv by Molecular Evolution of the Complementarity Determining Regions in the Center of the Antibody Binding Site," Journal of Molecular Biology, Nov. 8, 1996, 263(4):551-567.

Shields et al., "High resolution mapping of the binding site on human IgG1 for Fc gamma RI, Fc gamma RII, Fc gamma RIII, and FcRn and design of IgG1 variants with improved binding to the Fc gamma R," Journal of Biological Chemistry, Mar. 2, 2001, Epub Nov. 28, 2000, 276(9):6591-6604.

Shields et al., "Lack of fucose on human IgG1 N-linked oligosaccharide improves binding to human Fcgamma RIII and antibody-dependent cellular toxicity," Journal of Biological Chemistry Jul. 26, 2002, 277(30):26733-26740.

Shin et al., "Prospects for TIM3-Targeted Antitumor Immunotherapy," Cancer Research, Oct. 18, 2021, 71(21), 14 pages.

Shinkawa et al, "The absence of fucose but not the presence of galactose or bisecting N-acetylglucosamine of human IgG1 complex-type oligosaccharides shows the critical role of enhancing antibody-dependent cellular cytotoxicity," Journal of Biological Chemistry Jan. 31, 2003, Nov. 8, 2002, 278(5):3466-3473.

Sims et al., "A Humanized CD18 Antibody Can Block Function Without Cell Destruction," Journal of Immunology, Aug. 15, 1993, 151(4):2296-2308.

Steurer et al., "Ex Vivo Coating of Islet Cell Allografts with Murine CTLA4/Fc Promotes Graft Tolerance," The Journal of Immunology, Aug. 1, 1995, 155(3):1165-1174.

Tonegawa, "Somatic generation of antibody diversity," Nature, Apr. 14, 1983, 302(5909):575-581.

Urlaub et al., "Isolation of Chinese hamster cell mutants deficient in dihydrofolate reductase activity," Proceedings of the Natural Academy of Sciences, USA, Jul. 1980, 77(7):4216-4220.

Vaughn et al., "Structural basis of pH-dependent antibody binding by the neonatal Fc receptor," Structure, Jan. 15, 1998, 6(1):63-73.

Verhoeyen et al., "Reshaping Human Antibodies: Grafting an Antilysozyme Activity," Science, Mar. 25, 1988, 239(4847):1534-1536.

Waight et al.,"INCAGN02390, a novel antagonist antibody that targets the co-inhibitory receptor TIM-3," Abstract 3825, AACR Annual Meeting 2018; Apr. 14-18, 2018; Chicago, IL, 1 page.

Xu et al., "Diversity in the CDR3 region of V(H) is sufficient for most antibody specificities," Immunity, Jul. 2000, 13(1):37-45.

Yeung et al., "A therapeutic anti-VEGF antibody with increased potency independent of pharmacokinetic half-life," Cancer Research, Apr. 15, 2010, 70(8):3269-3277.

Acharya et al., "Tim-3 finds its place in the cancer immunotherapy landscape," Journal for ImmunoTherapy of Cancer, Jun. 29, 2020, 8:e000911, 11 pages.

Das et al., "Tim-3 and its role in regulating anti-tumor immunity," Immunol. Rev., Mar. 2017, 276(1):97-111.

* cited by examiner

SEQUENCE LISTING

```
<160> NUMBER OF SEQ ID NOS: 14

<210> SEQ ID NO 1
<211> LENGTH: 10
<212> TYPE: PRT
<213> ORGANISM: Rattus norvegicus

<400> SEQUENCE: 1

Gly Phe Ser Leu Thr Asn Tyr Gly Val Gly
1               5                   10

<210> SEQ ID NO 2
<211> LENGTH: 16
<212> TYPE: PRT
<213> ORGANISM: Rattus norvegicus

<400> SEQUENCE: 2

Arg Ser Ser Gln Ser Leu Ser Asp Ser Ala Gly Ile Thr Tyr Leu Tyr
1               5                   10                  15

<210> SEQ ID NO 3
<211> LENGTH: 16
<212> TYPE: PRT
<213> ORGANISM: Rattus norvegicus

<400> SEQUENCE: 3

Ile Met Thr Ser Gly Gly Ser Thr Tyr Tyr Asn Ser Ala Leu Arg Ala
1               5                   10                  15

<210> SEQ ID NO 4
<211> LENGTH: 7
<212> TYPE: PRT
<213> ORGANISM: Rattus norvegicus

<400> SEQUENCE: 4

Leu Ala Ser Asn Leu Gly Ser
1               5

<210> SEQ ID NO 5
<211> LENGTH: 11
<212> TYPE: PRT
<213> ORGANISM: Rattus norvegicus

<400> SEQUENCE: 5

Asp Gly Thr Thr Val Glu Thr Leu Phe Asp Tyr
1               5                   10

<210> SEQ ID NO 6
<211> LENGTH: 9
<212> TYPE: PRT
```

<213> ORGANISM: Rattus norvegicus

<400> SEQUENCE: 6

Met Gln Gly Ile His Val Pro Leu Thr
1               5

<210> SEQ ID NO 7
<211> LENGTH: 119
<212> TYPE: PRT
<213> ORGANISM: Rattus norvegicus

<400> SEQUENCE: 7

Gln Val Gln Leu Lys Glu Ser Gly Pro Gly Leu Val Gln Ser Ser Gln
1               5                   10                  15

Thr Leu Ser Leu Thr Cys Thr Val Ser Gly Phe Ser Leu Thr Asn Tyr
            20                  25                  30

Gly Val Gly Trp Ile Arg Gln Pro Pro Gly Lys Gly Leu Glu Trp Ile
        35                  40                  45

Ala Ile Met Thr Ser Gly Gly Ser Thr Tyr Tyr Asn Ser Ala Leu Arg
    50                  55                  60

Ala Arg Leu Asn Ile Asn Arg Asp Thr Ser Lys Ser Gln Val Phe Leu
65                  70                  75                  80

Glu Val Asn Ser Leu His Thr Glu Asp Thr Ala Thr Tyr Phe Cys Thr
                85                  90                  95

Arg Asp Gly Thr Thr Val Glu Thr Leu Phe Asp Tyr Trp Gly Gln Gly
            100                 105                 110

Leu Met Val Thr Val Ser Ser
        115

<210> SEQ ID NO 8
<211> LENGTH: 357
<212> TYPE: DNA
<213> ORGANISM: Rattus norvegicus

<400> SEQUENCE: 8
caggtgcagc tgaaagagtc aggacctggt ctggtgcagt cctcacagac tctgtctctc      60
acctgcactg tctctggatt ctcattaacc aactatggtg tagggtggat tcgccagcct     120
ccagggaagg gtctggagtg gattgcaata atgacaagtg gtggaagcac atattacaat     180
tcagctctca gagcccgact gaacatcaac agggacacct ccaagagcca agttttctta     240
gaagtgaaca gtctgcacac tgaagacaca gccacttact ctgtaccag ggatgggact      300
acggtagaaa ccctctttga ttactggggc caaggactca tggtcacagt ctcctca       357

<210> SEQ ID NO 9
<211> LENGTH: 112
<212> TYPE: PRT
<213> ORGANISM: Rattus norvegicus

<400> SEQUENCE: 9

Asp Val Val Leu Thr Gln Thr Pro Ser Thr Leu Ser Ala Ile Ile Gly
1               5                   10                  15

Gln Ser Val Ser Ile Ser Cys Arg Ser Ser Gln Ser Leu Ser Asp Ser
            20                  25                  30

Ala Gly Ile Thr Tyr Leu Tyr Trp Tyr Leu Gln Arg Pro Gly Gln Ser
        35                  40                  45

Pro Gln Leu Leu Ile Tyr Leu Ala Ser Asn Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Pro Glu Asp Leu Gly Val Tyr His Cys Met Gln Gly
                85                  90                  95

Ile His Val Pro Leu Thr Phe Gly Ser Gly Thr Lys Leu Glu Ile Lys
            100                 105                 110

<210> SEQ ID NO 10
<211> LENGTH: 336
<212> TYPE: DNA
<213> ORGANISM: Rattus norvegicus

<400> SEQUENCE: 10
gatgttgtgc tgacccagac tccatccaca ttatcggcta ttattggaca atcggtctcc      60
atctcttgca ggtcaagtca gagtctctca gatagtgctg gaatcaccta tttgtattgg     120
tatctacaga ggcctggcca atctccacag cttctaattt atctggcatc caacctggga     180
tctggggtcc ccaacaggtt cagtggcagt gggtcaggaa ctgatttcac actcaaaatc     240
agtggagtgg agcctgagga tttgggagtt tatcactgca tgcaaggaat ccatgttccg     300
ctcacgttcg gttctgggac caagctggag atcaaa                               336

<210> SEQ ID NO 11
<211> LENGTH: 119
<212> TYPE: PRT
<213> ORGANISM: Artificial Sequence
<220> FEATURE:
<223> OTHER INFORMATION: Synthetic

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

Gly Val Gly Trp Ile Arg Gln Pro Pro Gly Lys Gly Leu Glu Trp Ile
            35                  40                  45

Gly Ile Met Thr Ser Gly Gly Ser Thr Tyr Tyr Asn Ser Ala Leu Arg
50                  55                  60

Ala Arg Val Thr Ile Asn Arg Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Arg Asp Gly Thr Thr Val Glu Leu Phe Asp Tyr Trp Gly Gln Gly
            100                 105                 110

Thr Met Val Thr Val Ser Ser
        115

<210> SEQ ID NO 12
<211> LENGTH: 357
<212> TYPE: DNA
<213> ORGANISM: Artificial Sequence
<220> FEATURE:
<223> OTHER INFORMATION: Synthetic

<400> SEQUENCE: 12
caggtgcagc tgcaggagag cggccctgga ctggtgaagc ccagcgagac cctgtccctg      60
acctgcaccg tgtccggctt ctccctgacc aactacggcg tgggctggat caggcagcct     120
cctggaaagg gcctggagtg gatcggcatc atgacctccg gcggctccac ctactacaac     180

```
tccgccctga gggccagggt gaccatcaac agggacacct ccaagaacca gttctccctg      240
aagctgtcct ccgtgaccgc tgccgatacc gccgtgtact actgcaccag ggacggcacc      300
accgtggaga ccctgttcga ctactgggc cagggcacca tggtgaccgt gtcctcc          357
```

<210> SEQ ID NO 13
<211> LENGTH: 112
<212> TYPE: PRT
<213> ORGANISM: Artificial Sequence
<220> FEATURE:
<223> OTHER INFORMATION: Synthetic

<400> SEQUENCE: 13

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Ser Asp Ser
            20                  25                  30

Ala Gly Ile Thr Tyr Leu Tyr Trp Tyr Leu Gln Lys Pro Gly Gln Ser
        35                  40                  45

Pro Gln Leu Leu Ile Tyr Leu Ala Ser Asn Leu Gly Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Val Pro Leu Thr Phe Gly Gln Gly Thr Lys Leu Glu Ile Lys
            100                 105                 110
```

<210> SEQ ID NO 14
<211> LENGTH: 336
<212> TYPE: DNA
<213> ORGANISM: Artificial Sequence
<220> FEATURE:
<223> OTHER INFORMATION: Synthetic

<400> SEQUENCE: 14

```
gacatcgtga tgacccagac ccctctgtcc ctgtccgtga ccctggaca gcccgctagc      60 atctcctgca ggtcctccca gtccctgtcc gattccgccg gcatcaccta cctgtactgg      120
tacctgcaga agcctggcca gtccccccag ctgctgatct acctggcttc aacctgggc      180 tccggcgtgc ctgacaggtt ctccggatcc ggctccggca ccgacttcac cctgaagatc      240
tccagggtgg aggccgagga tgtgggcgtg tactactgca tgcagggcat ccacgtgccc      300
ctgaccttcg gccagggcac caagctggag atcaag                              336
```

ANTI-TIM-3 ANTIBODIES

PRIORITY CLAIM

The present application is a U.S. National Phase application, filed under 35 U.S.C. § 371(c), of International Application No. PCT/CN2019/078661, filed Mar. 19, 2019, which claims priority to, and the benefit of, PCT Application Number PCT/CN2018/079624, filed Mar. 20, 2018, the entire contents of each of which are herein incorporated by reference.

INCORPORATION OF THE SEQUENCE LISTING

The contents of the text file submitted electronically herewith are incorporated herein by reference in their entirety: a computer readable format copy of the Sequence Listing (filename: CCPI_014_01US_SeqList_ST25.txt, date recorded Sep. 15, 2020, file size 8 kb).

FIELD OF THE INVENTION

The present disclosure generally relates to novel anti-human TIM-3 antibodies.

BACKGROUND

T cell immunoglobulin mucin-3 (TIM-3), member of the TIM family, is a type I transmembrane protein that possesses an N-terminal Ig domain of the V type, followed by a mucin domain containing potential sites of glycosylation. TIM-3 is preferentially expressed on activated Th1 cells and cytotoxic CD8 T cells that secrete IFNγ, dendritic cells (DCs), monocytes and NK cells. It is an activation-induced inhibitory molecule and induces the apoptosis of Th1 cells, resulting in T cell exhaustion in chronic viral infection and cancer patients.

Four molecules have been reported as ligands of TIM-3, including carcinoembryonic antigen cell adhesion molecule 1 (CEACAM1), phosphatidylserine (PtdSer), High mobility group protein 1 (HMGB1), and Galectine-9 (Gal-9). Among these ligands, CEACAM1, HMGB1 as well as Gal-9 have been reported to negatively regulate immune response. A recent study has showed that CEACAM1, known to be expressed on activated T cells and involved in T cell inhibition, can form cis and trans interaction with TIM-3 to suppress anti-tumor T cell response. HMGB1 binds to DNA released by cells undergoing necrosis, and mediates the activation of innate cells through receptor for advanced glycation end (RAGE) products and/or Toll-like receptors. By binding to HMGB1, TIM-3 prevents the binding of HMGB1 to DNA, and therefore interferes the function of HMGB1 on activating the innate immune response in tumor tissue. Although the role of Gal-9 on human T cells is controversial, Gal-9 has been shown to bind to mouse TIM-3 and negatively regulate Th-1 immune response. Recently, leukocyte immunoglobulin-like receptor subfamily B member 2 (LILRB2) has been reported to interact with TIM-3 to regulate the function of DCs, macrophages and T cells. The blockage of TIM-3/LILRB2 interaction can enhance the activation of macrophages; increase T cell response and proliferation.

It has been suggested that TIM-3 may be a key immune checkpoint in tumor-induced immune suppression, as TIM-3 is expressed on the most suppressed or dysfunctional tumor-infiltrating lymphocytes (TILs) in preclinical models of both solid and hematologic malignancy, as well as patients with advanced melanoma, non-small cell lung cancer (NSCLC) or follicular B-cell non-Hodgkin lymphoma. In multiple preclinical tumor models, the treatment of anti-TIM-3 alone or in combination of other immune checkpoint therapy, such as anti-PD-1 can dramatically suppress the tumor growth.

There is a significant need for novel anti-TIM-3 antibodies.

BRIEF SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides isolated anti-TIM-3 antibodies or an antigen-binding fragments thereof, comprising:
a) 1, 2, or 3 heavy chain complementarity determining region (CDR) sequences selected from the group consisting of: SEQ ID NO: 1, SEQ ID NO: 3, and SEQ ID NO: 5; and/or
b) 1, 2, or 3 light chain CDR sequences selected from the group consisting of: SEQ ID NO: 2, SEQ ID NO: 4, and SEQ ID NO: 6.

In certain embodiments, the isolated anti-TIM-3 antibody or an antigen-binding fragment thereof comprises a heavy chain variable region comprising the 3 CDR sequences of SEQ ID NO: 1, SEQ ID NO: 3, and SEQ ID NO: 5.

In certain embodiments, the isolated anti-TIM-3 antibody or an antigen-binding fragment thereof comprises a light chain variable region comprising the 3 CDR sequences of SEQ ID NO: 2, SEQ ID NO: 4, and SEQ ID NO: 6.

In certain embodiments, the isolated anti-TIM-3 antibody or an antigen-binding fragment thereof comprises a heavy chain variable region comprising the 3 CDR sequences of SEQ ID NO: 1, SEQ ID NO: 3, and SEQ ID NO: 5; and a light chain variable region comprising the 3 CDR sequences of SEQ ID NO: 2, SEQ ID NO: 4, and SEQ ID NO: 6.

In certain embodiments, the isolated anti-TIM-3 antibody or an antigen-binding fragment thereof comprises a heavy chain variable region selected from the group consisting of SEQ ID NO: 7, SEQ ID NO: 11, and a homologous sequence thereof having at least 80% sequence identity yet retaining specific binding affinity to TIM-3.

In certain embodiments, the isolated anti-TIM-3 antibody or an antigen-binding fragment thereof comprises a light chain variable region selected from the group consisting of SEQ ID NO: 9, SEQ ID NO: 13, and a homologous sequence thereof having at least 80% sequence identity yet retaining specific binding affinity to TIM-3.

In certain embodiments, the isolated anti-TIM-3 antibody or an antigen-binding fragment thereof comprises:
a) a heavy chain variable region comprising SEQ ID NO: 7 and a light chain variable region comprising SEQ ID NO: 9; and
b) a heavy chain variable region comprising SEQ ID NO: 11 and a light chain variable region comprising SEQ ID NO: 13.

In certain embodiments, the isolated anti-TIM-3 antibody or an antigen-binding fragment thereof further comprises one or more amino acid residue substitutions or modifications yet retains specific binding affinity to TIM-3. In certain embodiments, at least one of the substitutions or modifications is in one or more of the CDR sequences, and/or in one or more of the heavy chain variable region or light chain variable region sequences but not in any of the CDR sequences.

In certain embodiments, the isolated anti-TIM-3 antibody or an antigen-binding fragment thereof further comprises an immunoglobulin constant region, optionally a constant region of immunoglobulin (Ig), or optionally of human Ig, or optionally of human IgG.

In certain embodiments, the isolated anti-TIM-3 antibody or an antigen-binding fragment thereof comprise a human IgG4 constant region comprising an amino acid substitution of S228P.

In certain embodiments, the isolated anti-TIM-3 antibody or an antigen-binding fragment thereof comprises a human IgG1 constant region comprising one or more amino acid substitution of L234F, L235E and/or P331S. In certain embodiments, the anti-TIM-3 antibody or an antigen-binding fragment thereof comprises a human IgG1 constant region in which Arg is inserted after position 236 along with L328R.

In certain embodiments, the isolated anti-TIM-3 antibody or an antigen-binding fragment thereof is humanized.

In certain embodiments, the isolated anti-TIM-3 antibody or an antigen-binding fragment thereof is a camelized single domain antibody, a diabody, a scFv, an scFv dimer, a BsFv, a dsFv, a (dsFv)$_2$, an Fv fragment, a Fab, a Fab', a F(ab')$_2$, a ds diabody, a nanobody, a domain antibody, scFv-Fc antibody, or a bivalent antibody.

In certain embodiments, the isolated anti-TIM-3 antibody or an antigen-binding fragment thereof is capable of specifically binding to human TIM-3 at a $K_D$ value of no more than $5\times10^{-9}$M (e.g. no more than $4\times10^{-9}$M, no more than $3\times10^{-9}$M, no more than $2\times10^{-9}$M, no more than $10^{-9}$M, no more than $5\times10^{-10}$ M, no more than $4\times10^{-10}$ M, no more than $3\times10^{-10}$ M, no more than $2\times10^{-10}$ M, no more than $10^{-10}$ M, no more than $5\times10^{-11}$M, no more than $4\times10^{-11}$M, no more than $3\times10^{-11}$M, no more than $2\times10^{-11}$M, or no more than $10^{-11}$M) as measured by surface plasmon resonance (SPR).

In certain embodiments, the isolated anti-TIM-3 antibody or an antigen-binding fragment thereof is capable of specifically binding to human TIM-3 expressed on a cell surface at an $EC_{50}$ of no more than 10 nM (e.g. 9 nM, 8 nM, 7 nM, 6 nM, 5 nM, 4 nM, 3 nM, 2 nM, 1 nM, 0.5 nM, 0.2 nM, 0.1 nM, 0.05 nM, or 0.01 nM) as measured by flow cytometry.

In certain embodiments, the isolated anti-TIM-3 antibody or an antigen-binding fragment thereof is capable of specifically binding to cynomolgus monkey TIM-3.

In certain embodiments, the isolated anti-TIM-3 antibody or an antigen-binding fragment thereof is linked to one or more conjugate moieties. In certain embodiments, the conjugate moiety comprises a clearance-modifying agent, a toxin, a detectable label, a chemotherapeutic agent, or purification moiety.

The present disclosure also provides herein an antibody or an antigen-binding fragment thereof, which competes for the same epitope with the antibody or antigen-binding fragment thereof provided herein.

The present disclosure also provides herein a pharmaceutical composition comprising the antibody or antigen-binding fragment thereof of provided herein, and a pharmaceutically acceptable carrier.

The present disclosure also provides herein an isolated polynucleotide encoding the antibody or an antigen-binding fragment thereof as provided herein. In certain embodiments, the isolated polynucleotide comprises a nucleotide sequence selecting from a group consisting of SEQ ID NO: 8, SEQ ID NO: 10, SEQ ID NO: 12, and SEQ ID NO: 14, and/or a homologous sequence thereof having at least 80% (e.g. at least 85%, 88%, 90%, 92%, 93%, 94%, 95%, 96%, 97%, 98%, or 99%) sequence identity, and/or a variant thereof having only degenerate substitutions.

The present disclosure also provides herein a vector comprising the isolated polynucleotide as provided herein.

The present disclosure also provides herein a host cell comprising the vector as provided herein.

The present disclosure also provides herein a method of expressing the antibody or antigen-binding fragment thereof of as provided herein, comprising culturing the host cell as provided herein under the condition at which the vector as provided herein is expressed.

The present disclosure also provides herein a method of treating a disease or condition in a subject that would benefit from modulation of TIM-3 activity, comprising administering to the subject a therapeutically effective amount of the antibody or antigen-binding fragment thereof or the pharmaceutical composition as provided herein. In certain embodiments, the disease or condition is a TIM-3 related disease or condition. In certain embodiments, the disease or condition is cancer, autoimmune disease, inflammatory disease, or infectious disease. In certain embodiments, the subject is human. In certain embodiments, the administration is via oral, nasal, intravenous, subcutaneous, sublingual, or intramuscular administration.

In certain embodiments, the cancer is lymphoma, basal cell carcinoma, biliary tract cancer, bladder cancer, bone cancer, brain and central nervous system cancer, breast cancer, peritoneal cancer, cervical cancer, uterine or endometrial cancer, choriocarcinoma, colon cancer, colorectal cancer, rectal cancer, connective tissue cancer, esophageal cancer, mesothelioma, nasopharyngeal cancer, eye cancer, head and neck cancer, anal cancer, gastrointestinal cancer, glioblastoma, intra-epithelial neoplasm, kidney or renal cancer, larynx cancer, leukemia, liver cancer, lung cancer, melanoma, myeloma, neuroblastoma, oral cavity cancer, germ cell cancer, ovarian cancer, pancreatic cancer, prostate cancer, retinoblastoma, rhabdomyosarcoma, salivary gland carcinoma, sarcoma, skin cancer, squamous cell cancer, stomach cancer, testicular cancer, thyroid cancer, or vulval cancer.

In certain embodiments, the disease or condition is B cell lymphoma, optionally Hodgkin lymphoma or non-Hodgkin lymphoma (NHL), wherein the NHL comprises: diffuse large B-cell lymphoma (DLBCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, Waldenstrom's Macroglobulinemia, chronic lymphocytic leukemia (CLL), acute lymphoblastic leukemia (ALL), hairy cell leukemia, chronic myeloblastic leukemia, and post-transplant lymphoproliferative disorder (PTLD), as well as abnormal vascular proliferation associated with phakomatoses, edema, and Meigs' syndrome.

The present disclosure also provides herein a method of modulating TIM-3 activity in a TIM-3-expressing cell, comprising exposing the TIM-3-expressing cell to the antibody or antigen-binding fragment thereof as provided herein.

The present disclosure also provides herein a method of detecting presence or amount of TIM-3 in a sample, comprising contacting the sample with the antibody or antigen-binding fragment thereof as provided herein, and determining the presence or the amount of TIM-3 in the sample.

The present disclosure also provides herein a method of diagnosing a TIM-3 related disease or condition in a subject, comprising: a) contacting a sample obtained from the subject with the antibody or antigen-binding fragment thereof as provided herein; b) determining presence or amount of TIM-3 in the sample; and c) correlating the presence or the amount of TIM-3 to existence or status of the TIM-3 related disease or condition in the subject.

The present disclosure also provides herein use of the antibody or antigen-binding fragment thereof as provided herein in the manufacture of a medicament for treating a TIM-3 related disease or condition in a subject.

The present disclosure also provides herein use of the antibody or antigen-binding fragment thereof as provided herein in the manufacture of a diagnostic reagent for diagnosing a TIM-3 related disease or condition.

The present disclosure also provides herein a kit comprising the antibody or antigen-binding fragment thereof as provided herein, useful in detecting TIM-3.

BRIEF DESCRIPTION OF FIGURES

FIG. 8 demonstrates that W3402-z3 can partially block the suppressive function of Tregs in regulating CD4+ T cell proliferation.

DETAILED DESCRIPTION OF THE INVENTION

Figure 1A:
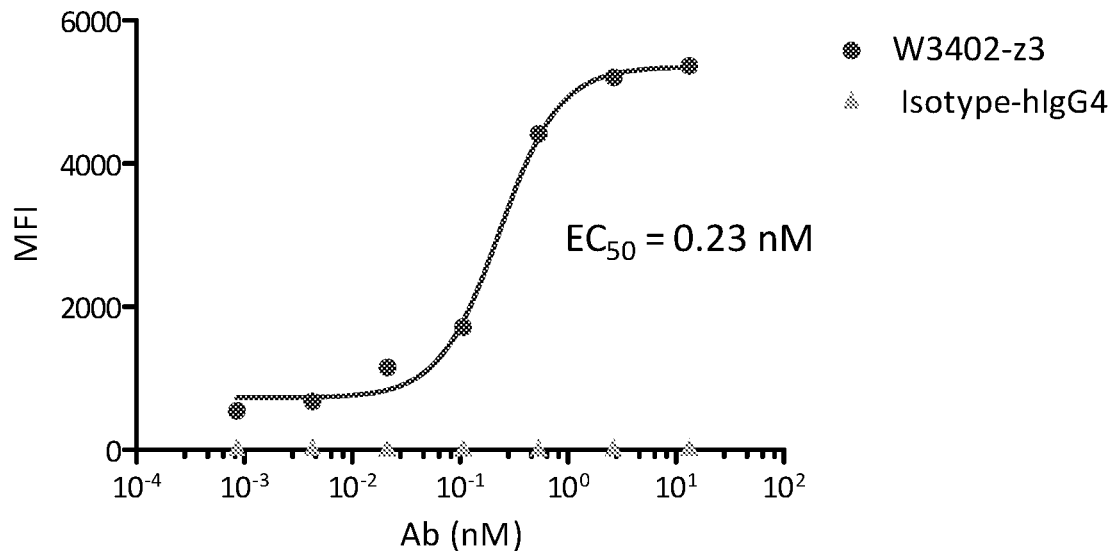
FIG. 1 shows binding of W3402-z3 to cell surface human TIM-3 (FIG. 1A) and cynomolgus monkey TIM-3 (FIG. 1B).

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, or monovalent antibody that binds to a specific antigen. A native intact antibody comprises two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as λ or κ, while each light chain consists of a variable region ($V_L$) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991); Marie-Paule Lefranc et al, Developmental and Comparative Immunology, 27: 55-77 (2003); Marie-Paule Lefranc et al, Immunome Research, 1(3), (2005); Marie-Paule Lefranc, Molecular Biology of B cells (second edition), chapter 26, 481-514, (2015)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

The term "bivalent" as used herein refers to an antibody or an antigen-binding fragment having two antigen-binding sites; the term "monovalent" refers to an antibody or an antigen-binding fragment having only one single antigen-binding site; and the term "multivalent" refers to an antibody or an antigen-binding fragment having multiple antigen-binding sites. In some embodiments, the antibody or antigen-binding fragment thereof is bivalent.

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a F(ab')$_2$, an Fv fragment, a disulfide stabilized Fv fragment (dsFv), a (dsFv)$_2$, a disulfide stabilized diabody (ds diabody), a single-chain antibody molecule (scFv), an scFv dimer (bivalent diabody), a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'. "Fv" with regard to an antibody refers to the smallest fragment of the antibody to bear the complete antigen-binding site. An Fv fragment consists of the variable region of a single light chain bound to the variable region of a single heavy chain.

A "dsFv" refers to a disulfide-stabilized Fv fragment that the linkage between the variable region of a single light chain and the variable region of a single heavy chain is a disulfide bond. In some embodiments, a "(dsFv)$_2$" comprises three peptide chains: two $V_H$ moieties linked by a peptide linker (e.g., a long flexible linker) and bound to two $V_L$ moieties, respectively, via disulfide bridges.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879(1988)).

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as antibody-dependent cell-mediated cytotoxicity (ADCC), and complement dependent cytotoxicity (CDC), but does not function in antigen binding.

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods. December 10; 231(1-2): 25-38 (1999); Muyldermans S., J Biotechnol. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature. June 3; 363(6428):446-8 (1993); Nguyen V K. et al. "Heavy-chain antibodies in Camelidae; a case of evolutionary innovation," Immunogenetics. April; 54(1):39-47 (2002); Nguyen V K. et al. Immunology. May; 109(1): 93-101 (2003)). The variable domain of a heavy chain antibody (VHH domain) represents the smallest known antigen-binding unit generated by adaptive immune responses (Koch-Nolte F. et al., FASEB J. November; 21(13):3490-8. Epub 2007 Jun. 15 (2007)).

A "nanobody" refers to an antibody fragment that consists of a VHH domain from a heavy chain antibody and two constant domains, CH2 and CH3.

"Diabodies" or "dAbs" includes small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigen (or epitope).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same antigen.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal, such as from mouse. In some embodiments, the non-human animal is a mammal, for example, a mouse, a rat, a rabbit, a goat, a sheep, a guinea pig, or a hamster.

The term "humanized" as used herein means that the antibody or antigen-binding fragment comprises CDRs derived from non-human animals, FR regions derived from human, and when applicable, the constant regions derived from human.

"TIM-3" as used herein, is derived from any vertebrate source, including mammals such as primates (e.g. humans, monkeys) and rodents (e.g., mice and rats). Exemplary sequence of human TIM-3 includes human TIM-3 protein (NCBI accession number GI: 18182535). Exemplary sequence of TIM-3 includes *Mus musculus* (mouse) TIM-3 protein (NCBI accession number GI: 18182531), *Rattus norvegicus* (rat) TIM-3 protein (NCBI accession number GI 39725405), and *Macaca fascicularis* (monkey) TIM-3 protein (NCBI accession number GI: 355750365).

The term "TIM-3" as used herein is intended to encompass any form of TIM-3, for example, 1) native unprocessed TIM-3 molecule, "full-length" TIM-3 chain or naturally occurring variants of TIM-3, including, for example, splice variants or allelic variants; 2) any form of TIM-3 that results from processing in the cell; or 3) full length, a fragment (e.g., a truncated form, an extracellular/transmembrane domain) or a modified form (e.g. a mutated form, a glycosylated/PEGylated, a His-tag/immunofluorescence fused form) of TIM-3 subunit generated through recombinant method.

The term "anti-TIM-3 antibody" refers to an antibody that is capable of specific binding TIM-3 (e.g. human or monkey TIM-3).

The term "specific binding" or "specifically binds" as used herein refers to a non-random binding reaction between two molecules, such as for example between an antibody and an antigen. In certain embodiments, the antibodies or antigen-binding fragments provided herein specifically bind to human and/or TIM-3 with a binding affinity ($K_D$) of $\leq 10^{-6}$ M (e.g., $\leq 5 \times 10^{-7}$M, $\leq 2 \times 10^{-7}$M, $\leq 10^{-7}$M, $\leq 5 \times 10^{-8}$M, $\leq 2 \times 10^{-8}$M, $\leq 10^{-8}$ M, $\leq 5 \times 10^{-9}$M, $\leq 4 \times 10^{-9}$M, $\leq 3 \times 10^{-9}$M, $\leq 2 \times 10^{-9}$ M, $\leq 10^{-9}$ M, $5 \times 10^{-10}$M, or $5 \times 10^{-11}$M). $K_D$ used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the $K_D$ value can be appropriately determined by using flow cytometry.

The ability to "block binding" or "compete for the same epitope" as used herein refers to the ability of an antibody or antigen-binding fragment to inhibit the binding interaction between two molecules (e.g. human TIM-3 and an anti-TIM-3 antibody) to any detectable degree. In certain embodiments, an antibody or antigen-binding fragment that blocks binding between two molecules inhibits the binding interaction between the two molecules by at least 85%, or at least 90%. In certain embodiments, this inhibition may be greater than 85%, or greater than 90%.

The term "epitope" as used herein refers to the specific group of atoms or amino acids on an antigen to which an antibody binds. Two antibodies may bind the same or a closely related epitope within an antigen if they exhibit competitive binding for the antigen. For example, if an antibody or antigen-binding fragment blocks binding of a reference antibody to the antigen by at least 85%, or at least 90%, or at least 95%, then the antibody or antigen-binding fragment may be considered to bind the same/closely related epitope as the reference antibody.

Those skilled in the art will recognize that it is possible to determine, without undue experimentation, if a given antibody binds to the same epitope as the antibody of present disclosure (e.g., rat monoclonal antibody W3402-2.131.17 (also referred to as "W3402" in the present disclosure), and humanized antibody W3402-2.131.17-z3 (also referred to as "W3402-z3" in the present disclosure) by ascertaining whether the former prevents the latter from binding to a TIM-3 antigen polypeptide. If the given antibody competes with the antibody of present disclosure, as shown by a decrease in binding by the antibody of present disclosure to the TIM-3 antigen polypeptide, then the two antibodies bind to the same, or a closely related, epitope. Or if the binding of a given antibody to the TIM-3 antigen polypeptide was inhibited by the antibody of present disclosure, then the two antibodies bind to the same, or a closely related, epitope.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "homologue" and "homologous" as used herein are interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An "isolated nucleic acid sequence" refers to the sequence of an isolated nucleic acid molecule. In certain embodiments, an "isolated antibody or antigen-binding fragment thereof" refers to the antibody or antigen-binding fragments having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the antibody or antigen-binding fragment thereof, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

A "TIM-3-related" disease or condition as used herein refers to any disease or condition caused by, exacerbated by, or otherwise linked to increased or decreased expression or activities of TIM-3. In some embodiments, the TIM-3 related condition is immune-related disorder, such as, for example, cancer, autoimmune disease, inflammatory disease or infectious disease.

"Cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells. Examples of cancer or tumors include hematological malignancies, oral carcinomas (for example of the lip, tongue or pharynx), digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In certain embodiments, the cancer is selected from ovarian cancer, breast cancer, head and neck cancer, renal cancer, bladder cancer, hepatocellular cancer, and colorectal cancer. In certain embodiments, the cancer is selected from a lymphoma, Hodgkin's lymphoma, non-Hodgkin's lymphoma and B-cell lymphoma.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-TIM-3 Antibody

The present disclosure provides anti-TIM-3 antibodies and antigen-binding fragments thereof comprising one or more (e.g. 1, 2, 3, 4, 5, or 6) CDR sequences of an anti-TIM-3 antibody W3402-2.131.17 (also referred to as "W3402" in the present disclosure).

"W3402" as used herein refers to a rat monoclonal antibody having a heavy chain variable region of SEQ ID NO: 7, and a kappa light chain variable region of SEQ ID NO: 9.

"W3402-z3" as used herein refers to a humanized monoclonal antibody having a heavy chain variable region of SEQ ID NO: 11, and a kappa light chain variable region of SEQ ID NO: 13.

Table 1 shows the CDR sequences of these 2 anti-TIM-3 antibodies. The heavy chain and light chain variable region sequences are also provided below in Table 2 and Table 3.

TABLE 1

| CDR amino acid sequences | | | | |
|---|---|---|---|---|
| | | CDR1 | CDR2 | CDR3 |
| W3402 and W3402-z3 | HCDR | SEQ ID NO: 1 GFSLTNYGVG | SEQ ID NO: 3 IMTSGGSTYYN SALRA | SEQ ID NO: 5 DGTTVETLFDY |
| | LCDR | SEQ ID NO: 2 RSSQSLSDSAGIT YLY | SEQ ID NO: 4 LASNLGS | SEQ ID NO: 6 MQGIHVPLT |

TABLE 2

| Variable region amino acid sequences | | |
|---|---|---|
| | VH | VL |
| W3402 | SEQ ID NO: 7 QVQLKESGPGLVQSSQTLSL TCTVSGFSLTNYGVGWIRQP PGKGLEWIAIMTSGGSTYYN SALRARLNINRDTSKSQVFL EVNSLHTEDTATYFCTRDGT TVETLFDYWGQGLMVTVSS | SEQ ID NO: 9 DVVLTQTPSTLSAIIGQSVSIS CRSSQSLSDSAGITYLYWYLQR PGQSPQLLIYLASNLGSGVPNR FSGSGSGTDFTLKISGVEPEDL GVYHCMQGIHVPLTFGSGTKLE IK |

TABLE 2-continued

Variable region amino acid sequences

| | VH | VL |
|---|---|---|
| W3402-z3 | SEQ ID NO: 11<br>QVQLQESGPGLVKPSETLSL<br>TCTVSGFSLTNYGVGWIRQP<br>PGKGLEWIGIMTSGGSTYYN<br>SALRARVTINRDTSKNQFSL<br>KLSSVTAADTAVYYCTRDG<br>TTVETLFDYWGQGTMVTVS<br>S | SEQ ID NO: 13<br>DIVMTQTPLSLSVTPGQPASIS<br>CRSSQSLSDSAGITYLYWYLQK<br>PGQSPQLLIYLASNLGSGVPDR<br>FSGSGSGTDFTLKISRVEAEDV<br>GVYYCMQGIHVPLTFGQGTKLE<br>IK |

TABLE 3

Variable region nucleotide sequences

| | VHnu | VLnu |
|---|---|---|
| W3402 | SEQ ID NO: 8<br>caggtgcagctgaaagagtcaggacctggt<br>ctggtgcagtcctcacagactctgtctctcac<br>ctgcactgtctctggattctcattaaccaacta<br>tggtgtagggtggattcgccagcctccagg<br>gaagggtctggagtggattgcaataatgaca<br>agtggtggaagcacatattacaattcagctct<br>cagagcccgactgaacatcaacagggaca<br>cctccaagagccaagtttttcttagaagtgaac<br>agtctgcacactgaagacacagccacttact<br>tctgtaccagggatgggactacggtagaaa<br>ccctctttgattactggggccaaggactcatg<br>gtcacagtctcctca | SEQ ID NO: 10<br>gatgttgtgctgacccagactccatccacattatcg<br>gctattattggacaatcggtctccatctcttgcaggt<br>caagtcagagtctctcagatagtgctggaatcacct<br>atttgtattggtatctacagaggcctggccaatctcc<br>acagcttctaatttatctggcatccaacctgggatct<br>ggggtccccaacaggttcagtggcagtgggtcag<br>gaactgatttcacactcaaaatcagtggagtggag<br>cctgaggatttgggagtttatcactgcatgcaagga<br>atccatgttccgctcacgttcggttctgggaccaag<br>ctggagatcaaa |
| W3402-z3 | SEQ ID NO: 12<br>caggtgcagctgcaggagagcggccctgg<br>actggtgaagcccagcgagaccctgtccct<br>gacctgcaccgtgtccggcttctccctgacc<br>aactacggcgtgggctggatcaggcagcct<br>cctggaaagggcctggagtggatcggcatc<br>atgacctccggcggctccacctactacaact<br>ccgccctgaggggccagggtgaccatcaac<br>agggacacctccaagaaccagttctccctga<br>agctgtcctccgtgaccgctgccgataccgc<br>cgtgtactactgcaccagggacggcaccac<br>cgtggagacctgttcgactactggggcca<br>gggcaccatggtgaccgtgtcctcc | SEQ ID NO: 14<br>gacatcgtgatgacccagacccctctgtccctgtcc<br>gtgacccctggacagcccgctagcatctcctgcag<br>gtcctcccagtccctgtccgattccgccggcatcac<br>ctacctgtactggtacctgcagaagcctggccagt<br>cccccagctgctgatctacctggcttccaacctgg<br>gctccggcgtgcctgacaggttctccggatccgg<br>ctccggcaccgacttcaccctgaagatctccaggg<br>tggaggccgaggatgtgggcgtgtactactgcat<br>gcagggcatccacgtgcccctgaccttcggccag<br>ggcaccaagctggagatcaag |

CDRs are known to be responsible for antigen binding, however, it has been found that not all of the 6 CDRs are indispensable or unchangeable. In other words, it is possible to replace or change or modify one or more CDRs in SEQ ID NOs: 1-6, yet substantially retain the specific binding affinity to TIM-3.

In certain embodiments, the anti-TIM-3 antibodies and the antigen-binding fragments provided herein comprise a heavy chain CDR3 sequence of SEQ ID NO: 5. Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81). The diversity in the heavy chain CDR3 is sufficient to produce most antibody specificities (Xu J L, Davis M M. Immunity. 13:37-45) as well as desirable antigen-binding affinity (Schier R, etc. J Mol Biol. 263:551-67).

In certain embodiments, the antibodies and antigen-binding fragments thereof provided herein comprise suitable framework region (FR) sequences, as long as the antibodies and antigen-binding fragments thereof can specifically bind to TIM-3. The CDR sequences provided in Table 1 are obtained from rat antibodies, but they can be grafted to any suitable FR sequences of any suitable species such as mouse, human, rat, rabbit, among others, using suitable methods known in the art such as recombinant techniques.

In certain embodiments, the antibodies and antigen-binding fragments thereof provided herein are humanized. A humanized antibody or antigen-binding fragment is desirable in its reduced immunogenicity in human. A humanized antibody is chimeric in its variable regions, as non-human CDR sequences are grafted to human or substantially human FR sequences. Humanization of an antibody or antigen-binding fragment can be essentially performed by substituting the non-human (such as murine) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Suitable human heavy chain and light chain variable domains can be selected to achieve this purpose using methods known in the art. In an illustrative example, "best-fit" approach can be used, where a non-human (e.g. rodent) antibody variable domain sequence is screened or BLASTed against a database of known human variable domain sequences, and the human sequence closest to the non-human query sequence is identified and used as the human scaffold for grafting the non-human CDR sequences (see, for example, Sims et al, (1993) J. Immunol. 151:2296; Chothia et al. (1987) J. Mot. Biol. 196:901). Alternatively, a framework derived from the consensus sequence of all human antibodies may be used for the grafting of the non-human CDRs (see, for example, Carter et at. (1992) Proc. Natl. Acad. Sci. USA, 89:4285; Presta et al. (1993) J. Immunol., 151:2623).

In certain embodiments, the humanized antibodies or antigen-binding fragments provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived different human immunoglobulin genes, for example, FR sequences derived from one human antibody and constant region from another human antibody. In some embodiments, the humanized antibody or antigen-binding fragment comprise human FR1-4.

In certain embodiments, the humanized antibodies and antigen-binding fragment thereof provided herein comprise one or more FR sequences of W3402-z3.

The exemplary humanized anti-TIM-3 antibody W3402-z3 retains the specific binding affinity to TIM-3-expressing cell, and are at least comparable to, or even better than, the parent rat antibodies in that aspect. The exemplary humanized antibody retained its functional interaction with TIM-3-expressing cell, such as CD4$^+$ T cells, in that it can trigger activated CD4$^+$ T cell cytokine release of IFNgamma and IL-2, and partially block the suppressive function of Tregs in regulating CD4$^+$ T cell proliferation.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody or its fragment closely approximate the non-human parent antibody structure. In certain embodiments, the humanized antibody or antigen-binding fragment provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains.

In certain embodiments, the antibodies and antigen-binding fragments thereof provided herein comprise a heavy chain variable domain sequence selected from the group consisting of SEQ ID NO: 7 or SEQ ID NO: 11. In certain embodiments, the antibodies and antigen-binding fragments thereof provided herein comprise a light chain variable domain sequence selected from the group consisting of SEQ ID NO: 9 or SEQ ID NO: 13.

In some embodiments, the anti-TIM-3 antibodies and the antigen-binding fragments provided herein comprise all or a portion of the heavy chain variable domain and/or all or a portion of the light chain variable domain. In one embodiment, the anti-TIM-3 antibodies and the antigen-binding fragments provided herein is a single domain antibody which consists of all or a portion of the heavy chain variable domain provided herein. More information of such a single domain antibody is available in the art (see, e.g., U.S. Pat. No. 6,248,516).

In certain embodiments, the anti-TIM-3 antibodies and the fragments thereof provided herein further comprise an immunoglobulin constant region. In some embodiments, an immunoglobulin constant region comprises a heavy chain and/or a light chain constant region. The heavy chain constant region comprises CH1, hinge, and/or CH2-CH3 regions. In certain embodiments, the heavy chain constant region comprises an Fc region. In certain embodiments, the light chain constant region comprises Cκ or Cλ.

In some embodiments, the anti-TIM3 antibodies and antigen-binding fragments thereof provided herein have a constant region of an immunoglobulin (Ig), optionally a human Ig, optionally a human IgG. In certain embodiments, the anti-TIM3 antibodies and antigen-binding fragments thereof provided herein comprises a constant region of IgG1 isotype, which could induce ADCC or CDC, or a constant region of IgG4 or IgG2 isotype, which has reduced or depleted effector function. Effector functions can be evaluated using various assays such as Fc receptor binding assay, C1q binding assay, and cell lysis assay.

Binding affinity of the antibody and antigen-binding fragment provided herein can be represented by K$_D$ value, which represents the ratio of dissociation rate to association rate ($k_{off}/k_{on}$) when the binding between the antigen and antigen-binding molecule reaches equilibrium. The antigen-binding affinity (e.g. K$_D$) can be appropriately determined using suitable methods known in the art, including, for example, flow cytometry assay. In some embodiments, binding of the antibody to the antigen at different concentrations can be determined by flow cytometry, the determined mean fluorescence intensity (MFI) can be firstly plotted against antibody concentration, K$_D$ value can then be calculated by fitting the dependence of specific binding fluorescence intensity (Y) and the concentration of antibodies (X) into the one site saturation equation: $Y=B_{max}*X/(K_D+X)$ using Prism version 5 (GraphPad Software, San Diego, CA), wherein B$_{max}$ refers to the maximum specific binding of the tested antibody to the antigen.

In some embodiments, the anti-TIM-3 antibodies and antigen-binding fragments thereof provided herein are capable of specifically binding to human TIM-3 with a binding affinity (K$_D$) of no more than 5×10$^{-9}$M, no more than 4×10$^{-9}$M, no more than 3×10$^{-9}$M, no more than 2×10$^{-9}$M, no more than 10$^{-9}$M, no more than 5×10$^{-10}$ M, no more than 4×10$^{-10}$ M, no more than 3×10$^{-10}$M, no more than 2×10$^{-10}$M, no more than 10$^{-10}$ M, no more than 5×10$^{-11}$ M, or no more than 4×10$^{-11}$ M as measured by surface plasmon resonance (SPR).

In certain embodiments, the anti-TIM-3 antibodies and antigen-binding fragments thereof provided herein cross-react with cynomolgus monkey TIM-3.

Binding of the antibodies to human TIM-3 can also be represented by "half maximal effective concentration" (EC$_{50}$) value, which refers to the concentration of an antibody where 50% of its maximal effect (e.g., binding or inhibition etc.) is observed. The EC$_{50}$ value can be measured by methods known in the art, for example, sandwich assay such as ELISA, Western Blot, flow cytometry assay, and other binding assay. In certain embodiments, the antibodies and the fragments thereof provided herein specifically bind to human TIM-3 at an EC$_{50}$ (i.e. 50% binding concentration) of no more than 0.25 nM, no more than 0.3 nM, no more than 0.35 nM, no more than 0.4 nM no more than 0.45 nM, no more than 0.5 nM, no more than 0.6 nM, no more than 0.7 nM, no more than 0.8 nM no more than 0.9 nM, no more than 1 nM, no more than 1.5 nM, no more than 2 nM, no more than 2.5 nM no more than 5 nM by flow cytometry.

In certain embodiments, the antibodies and antigen-binding fragments thereof bind to cynomolgus monkey TIM-3 with a binding affinity similar to that of human TIM-3. For example, binding of the exemplary antibody W3402-z3 to cynomolgus monkey TIM-3 is at a similar EC$_{50}$ value to that of human TIM-3.

In certain embodiments, the antibodies and the fragments thereof provided herein specifically bind to cynomolgus monkey TIM-3 with an EC$_{50}$ of no more than 0.35 nM, no more than 0.4 nM, no more than 0.45 nM, no more than 0.5 nM, no more than 0.6 nM, no more than 0.7 nM, no more than 0.8 nM no more than 0.9 nM, no more than 1 nM, no more than 1.5 nM, no more than 2 nM, no more than 2.5 nM no more than 5 nM by flow cytometery assay.

In certain embodiments, the antibodies and the fragments thereof provided herein have a specific binding affinity to human TIM-3 which is sufficient to provide for diagnostic and/or therapeutic use.

In certain embodiments, the antibodies and the fragments thereof provided herein inhibit binding of TIM-3 to its ligand and thereby providing biological activity including, for example, inducing cytokine production from the activated T cells (such as CD4$^+$ T cells and CD8$^+$ T cells), inducing proliferation of activated T cells (such as CD4$^+$ T cells and CD8$^+$ T cells), and reversing T reg's suppressive function. Exemplary cytokines include IL-2 and IFNγ. The term "IL-2" refers to interleukin 2, a type of cytokine signaling molecule in the immune system that regulates the activities of white blood cells (e.g. leukocytes). The term "Interferon gamma (IFNγ)" is a cytokine that is produced by natural killer (NK), NK T cells, CD4$^+$ and CD8$^+$ T cells, which is a critical activator of macrophages and inducer of major histocompatibility complex (MHC) molecule expression. The cytokine production can be determined using methods known in the art, for example, by ELISA. Methods can also be used to detect proliferation of T cells, including [$^3$H] thymidine incorporation assay.

The antibodies or antigen-binding fragments thereof provided herein can be a monoclonal antibody, polyclonal antibody, humanized antibody, chimeric antibody, recombinant antibody, labeled antibody, bivalent antibody, or anti-idiotypic antibody. A recombinant antibody is an antibody prepared in vitro using recombinant methods rather than in animals.

Antibody Variants

The antibodies and antigen-binding fragments thereof provided herein also encompass various variants thereof. In certain embodiments, the antibodies and antigen-binding fragments thereof encompasses various types of variants of an exemplary antibody provided herein, i.e., W3402 and W3402-z3.

In certain embodiments, the antibody variants comprise one or more modifications or substitutions in one or more CDR sequences as provided in Table 1, one or more variable region sequences (but not in any of the CDR sequences) provided in Table 2, and/or the constant region (e.g. Fc region). Such variants retain specific binding affinity to TIM-3 of their parent antibodies, but have one or more desirable properties conferred by the modification(s) or substitution(s). For example, the antibody variants may have improved antigen-binding affinity, improved productivity, improved stability, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation (e.g. one or more introduced cysteine residues).

The parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g., charged residues such as Arg, Asp, His, Lys, and Glu) can be identified and replaced by a neutral or negatively charged amino acid (e.g., alanine or polyalanine), and the modified antibodies are produced and screened for the interested property. If substitution at a particular amino acid location demonstrates an interested functional change, then the position can be identified as a potential residue for modification or substitution. The potential residues may be further assessed by substituting with a different type of residue (e.g. cysteine residue, positively charged residue, etc.).

Affinity Variant

Affinity variant may contain modifications or substitutions in one or more CDR sequences as provided in Table 1, one or more FR sequences, or the heavy or light chain variable region sequences provided in Table 2. FR sequences can be readily identified by a skilled person in the art based on the CDR sequences in Table 1 and variable region sequences in Table 2, as it is well-known in the art that a CDR region is flanked by two FR regions in the variable region. The affinity variants retain specific binding affinity to TIM-3 of the parent antibody, or even have improved TIM-3 specific binding affinity over the parent antibody. In certain embodiments, at least one (or all) of the substitution(s) in the CDR sequences, FR sequences, or variable region sequences comprises a conservative substitution.

A skilled artisan will understand that in the CDR sequences and variable region sequences provided in Table 1 and Table 2, one or more amino acid residues may be substituted yet the resulting antibody or antigen-binding fragment still retain the binding affinity to TIM-3, or even have an improved binding affinity. Various methods known in the art can be used to achieve this purpose. For example, a library of antibody variants (such as Fab or scFv variants) can be generated and expressed with phage display technology, and then screened for the binding affinity to human TIM-3. For another example, computer software can be used to virtually simulate the binding of the antibodies to human TIM-3, and identify the amino acid residues on the antibodies which form the binding interface. Such residues may be either avoided in the substitution so as to prevent reduction in binding affinity, or targeted for substitution to provide for a stronger binding.

In certain embodiments, the affinity variant provided herein comprises one or more amino acid residue substitutions in one or more CDR sequences, and/or one or more FR sequences. In certain embodiments, an affinity variant comprises no more than 10, 9, 8, 7, 6, 5, 4, 3, 2, or 1 substitutions in the CDR sequences and/or FR sequences in total.

In certain embodiments, the anti-TIM-3 antibodies and antigen-binding fragments thereof comprise 1, 2, or 3 CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to TIM-3 at a level similar to or even higher than its parent antibody.

In certain embodiments, the anti-TIM-3 antibodies and antigen-binding fragments thereof comprise one or more variable region sequences having at least 80% (e.g. at least 85%, 88%, 90%, 91%, 92%, 93%, 94%, 95%, 96%, 97%, 98%, 99%) sequence identity to that (or those) listed in Table 2, and in the meantime retain the binding affinity to TIM-3 at a level similar to or even higher than its parent antibody. In some embodiments, a total of 1 to 10 amino acids have been substituted, inserted, or deleted in a variable region sequence listed in Table 2. In some embodiments, the substitutions, insertions, or deletions occur in regions outside the CDRs (e.g., in the FRs).

Glycosylation Variant

The anti-TIM-3 antibodies and antigen-binding fragments provided herein also encompass a glycosylation variant, which can be obtained to either increase or decrease the extent of glycosylation of the antibody or antigen binding fragment.

The antibody or antigen binding fragment thereof may comprise one or more amino acid residues with a side chain to which a carbohydrate moiety (e.g. an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence in the is substituted. A new glycosylation site can be created in a similar way by introducing such a tripeptide sequence or serine or threonine residue.

Cysteine-Engineered Variant

The anti-TIM-3 antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with for example, a cytotoxic and/or imaging compound, a label, or a radioisoptype among others, at the site of the engineered cysteine, through for example a maleimide or haloacetyl. Methods for engineering antibodies or antigen-binding fragments to introduce free cysteine residues are known in the art, see, for example, WO2006/034488.

Fe Variant

The anti-TIM-3 antibodies and antigen-binding fragments provided herein also encompass an Fc variant, which comprises one or more amino acid residue modifications or substitutions at its Fc region and/or hinge region.

In certain embodiments, the anti-TIM-3 antibodies or antigen-binding fragments comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody and antigen-binding fragment thereof to improve binding affinity with FcRn are well-known in the art, see, for example, Vaughn, D. et al, Structure, 6(1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70: 3269-3277 (2010); and Hinton, P. et al, J. Immunology, 176:346-356 (2006).

In certain embodiments, the anti-TIM-3 antibodies or antigen-binding fragments comprise one or more amino acid substitution(s) that alters the antibody-dependent cellular cytotoxicity (ADCC). Certain amino acid residues at the Fc region (e.g. at the lower hinge and/or CH2 domain) can be substituted to provide for altered (e.g. enhanced or diminished or depleted) ADCC activity. Alternatively or additionally, carbohydrate structures on the antibody can be changed to alter (e.g. enhance, diminish or deplete) ADCC activity.

Methods of altering ADCC activity by antibody engineering have been described in the art, see for example, Shields R L. et al., J Biol Chem. 2001. 276(9): 6591-604; Idusogie E E. et al., J Immunol. 2000.164(8):4178-84; Steurer W. et al., J Immunol. 1995, 155(3): 1165-74; Idusogie E E. et al., J Immunol. 2001, 166(4): 2571-5; Lazar G A. et al., PNAS, 2006, 103(11): 4005-4010; Ryan M C. et al., Mol. Cancer Ther., 2007, 6: 3009-3018; Richards J O. et al., Mol Cancer Ther. 2008, 7(8): 2517-27; Shields R. L. et al, J. Biol. Chem, 2002, 277: 26733-26740; Shinkawa T. et al, J. Biol. Chem, 2003, 278: 3466-3473; and Oganesyan V. et al, Acta Crystallogr D Biol Crystallogr. 2008, 64: 700-704; Chu S Y. et al, Mol Immunol. 2008, 45: 3926-3933.

Different sets of substitutions may be employed to eliminate the IgG1 effector function. For example, L234F/L235E/P331S can dramatically decrease the binding between IgG1-Fc to C1q, CD64, CD32A and CD16 (Oganesyan V. et al, Acta Crystallogr D Biol Crystallogr. 2008, 64: 700-704). Also, IgG1-Fc carries the ˆ236R/L238R modification, which has an Arg inserted after position 236 along with L328R, showed profound decrease in binding activity of IgG1-Fc to the Fc gamma receptors (Chu S Y. et al, Mol Immunol. 2008, 45: 3926-3933).

In certain embodiments, the anti-TIM-3 antibodies or antigen-binding fragments comprise one or more amino acid substitution(s) that alters Complement Dependent Cytotoxicity (CDC), for example, by improving or diminishing C1q binding and/or CDC (see, for example, WO99/51642; Duncan & Winter Nature 322:738-40 (1988); U.S. Pat. Nos. 5,648,260; 5,624,821); and WO94/29351 concerning other examples of Fc region variants.

In certain embodiments, the anti-TIM-3 antibodies or antigen-binding fragments comprise a human IgG4 constant region in which the $228^{th}$ amino acid residue is altered, for example from Ser228Pro (S228P, which may prevent or reduce strand exchange), and/or the $235^{th}$ amino acid residue is altered, for example from Leu235Glu (L235E, which may alter Fc receptor interactions.

In certain embodiments, the anti-TIM-3 antibodies or antigen-binding fragments comprise a human IgG1 constant region in which the $234^{th}$, $235^{th}$, or $331^{st}$ amino acid residue is altered, for example, to introduce one or more amino acid substation of L234F, L235E and/or P331S. In certain embodiments, the anti-TIM-3 antibodies or antigen-binding fragments comprise a human IgG1 constant region in which Arg inserted after position 236 along with L328R.

In certain embodiments, the anti-TIM-3 antibodies or antigen-binding fragments comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g., as described in U.S. Pat. No. 5,731,168.

Antigen-Binding Fragments

Provided herein are also anti-TIM-3 antigen-binding fragments. Various types of antigen-binding fragments are known in the art and can be developed based on the anti-TIM-3 antibodies provided herein, including for example, the exemplary antibodies whose CDR and variable sequences are shown in Tables 1 and 2, and their different variants (such as affinity variants, glycosylation variants, Fc variants, cysteine-engineered variants and so on).

In certain embodiments, an anti-TIM-3 antigen-binding fragment provided herein is a camelid single domain antibody, a diabody, a single chain Fv fragment (scFv), an scFv dimer, a BsFv, a dsFv, a (dsFv)$_2$, an Fv fragment, a Fab, a Fab', a F(ab')$_2$, a ds diabody, a nanobody, a domain antibody, a single domain antibody, or a bivalent domain antibody.

Various techniques can be used for the production of such antigen-binding fragments. Illustrative methods include, enzymatic digestion of intact antibodies (see, e.g., Morimoto et al., Journal of Biochemical and Biophysical Methods 24:107-117 (1992); and Brennan et al., Science, 229:81 (1985)), recombinant expression by host cells such as E. Coli (e.g. for Fab, Fv and ScFv antibody fragments), screening from a phage display library as discussed above (e.g. for ScFv), and chemical coupling of two Fab'-SH fragments to form F(ab')$_2$ fragments (Carter et al., Bio/Technology 10:163-167 (1992)). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. scFv may be fused to an effector protein at either the amino or the carboxyl terminus to provide for a fusion protein (see, for example, Antibody Engineering, ed. Borrebaeck).

Conjugates

In some embodiments, the anti-TIM-3 antibodies and antigen-binding fragments thereof further comprise a conjugate moiety. The conjugate moiety can be linked to the antibodies and antigen-binding fragments thereof. A conjugate moiety is a non-proteinaceous moiety that can be attached to the antibody or antigen-binding fragment thereof. It is contemplated that a variety of conjugate moieties may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugate moieties may be linked to the antibodies or antigen-binding fragments by covalent binding, affinity binding, intercalation, coordinate binding, complexation, association, blending, or addition, among other methods.

In certain embodiments, the antibodies and antigen-binding fragments disclosed herein may be engineered to contain specific sites outside the epitope binding portion that may be utilized for binding to one or more conjugate moieties. For example, such a site may include one or more reactive amino acid residues, such as for example cysteine or histidine residues, to facilitate covalent linkage to a conjugate moiety.

In certain embodiments, the antibodies may be linked to a conjugate moiety indirectly, or through another conjugate moiety. For example, the antibody or antigen-binding fragments may be conjugated to biotin, then indirectly conjugated to a second conjugate moiety that is conjugated to avidin. The conjugate moiety can be a clearance-modifying agent, a toxin (e.g., a chemotherapeutic agent), a detectable label (e.g., a radioactive isotope, a lanthanide, a luminescent label, a fluorescent label, or an enzyme-substrate label), or purification moiety.

A "toxin" can be any agent that is detrimental to cells or that can damage or kill cells. Examples of toxin include, without limitation, taxol, cytochalasin B, gramicidin D, ethidium bromide, emetine, mitomycin, etoposide, tenoposide, vincristine, MMAE, MMAF, DM1, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), a topoisomerase inhibitor, and a tubulin-binders.

Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides), luminescent labels, chromophoric moiety, digoxigenin, biotin/avidin, a DNA molecule or gold for detection.

In certain embodiments, the conjugate moiety can be a clearance-modifying agent which helps increase half-life of the antibody. Illustrative example include water-soluble polymers, such as PEG, carboxymethylcellulose, dextran, polyvinyl alcohol, polyvinyl pyrrolidone, copolymers of ethylene glycol/propylene glycol, and the like. The polymer may be of any molecular weight, and may be branched or unbranched. The number of polymers attached to the antibody may vary, and if more than one polymer are attached, they can be the same or different molecules.

In certain embodiments, the conjugate moiety can be a purification moiety such as a magnetic bead.

In certain embodiments, the antibodies and antigen-binding fragments thereof provided herein is used for a base for a conjugate moiety.

Polynucleotides and Recombinant Methods

The present disclosure provides isolated polynucleotides that encode the anti-TIM-3 antibodies and antigen-binding fragments thereof.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

In certain embodiments, the isolated polynucleotides comprise one or more nucleotide sequences as shown in SEQ ID NO: 8, 10, 12, and/or 14, and/or a homologous sequence thereof having at least 80% (e.g. at least 85%, 88%, 90%, 92%, 93%, 94%, 95%, 96%, 97%, 98%, or 99%) sequence identity, and/or a variant thereof having only degenerate substitutions, and encodes the variable region of the exemplary antibodies provided herein. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The isolated polynucleotide that encodes the anti-TIM-3 antibodies and antigen-binding fragments thereof (e.g. including the sequences as shown in Table 3) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

The present disclosure provides vectors (e.g., expression vectors) containing the nucleic acid sequence provided herein encoding the antibodies or antigen-binding fragments, at least one promoter (e.g., SV40, CMV, EF-1a) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-TIM-3 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-TIM-3 antibody production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The anti-TIM-3 antibodies and antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., *J. Immunol. Meth.* 62:1-13 (1983)). Protein G is recommended for all mouse isotypes and for human gamma3 (Guss et al., *EMBO J.* 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Composition

The present disclosure further provides pharmaceutical compositions comprising the anti-TIM-3 antibodies or antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxyanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-TIM-3 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Methods of Use

The present disclosure also provides therapeutic methods comprising: administering a therapeutically effective amount of the antibody or antigen-binding fragment as provided herein to a subject in need thereof, thereby treating or preventing a TIM-3-related condition or a disorder. In some embodiment, the TIM-3-related condition or a disorder is cancer, autoimmune disease, inflammatory disease, or infectious disease. In some embodiment, the TIM-3-related condition or a disorder is solid tumor.

Examples of cancer include but are not limited to, cancer is lymphoma, bladder cancer, bone cancer, brain and central nervous system cancer, breast cancer, uterine or endometrial cancer, rectal cancer, esophageal cancer, head and neck cancer, anal cancer, gastrointestinal cancer, intra-epithelial neoplasm, kidney or renal cancer, leukemia, liver cancer, lung cancer (e.g. non-small cell lung cancer and small cell lung cancer), melanoma, myeloma, pancreatic cancer, prostate cancer, sarcoma, skin cancer, squamous cell cancer, stomach cancer, testicular cancer, vulval cancer, cancer of the endocrine system, cancer of the parathyroid gland, cancer of the adrenal gland, penile carcinoma, solid tumors of childhood, tumor angiogenesis, spinal axis tumor, pituitary adenoma, or epidermoid cancer.

Examples of autoimmune diseases include, but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Examples of infectious disease include, but are not limited to, fungus infection, parasite/protozoan infection or chronic viral infection, for example, malaria, coccidioiodmycosis immitis, histoplasmosis, onychomycosis, aspergilosis, blastomycosis, candidiasis albicans, paracoccidioiomycosis, microsporidiosis, Acanthamoeba keratitis, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, Trichuriasis, Trypanosomiasis, helminth infection, infection of hepatitis B (HBV), hepatitis C (HCV), herpes virus, Epstein-Barr virus, HIV, cytomegalovirus, herpes simplex virus type I, herpes simplex virus type II, human papilloma virus, adenovirus, human immunodeficiency virus I, human immunodeficiency virus II, Kaposi West sarcoma associated herpes virus epidemics, thin ring virus (Torquetenovirus), human T lymphotrophic viruse I, human T lymphotrophic viruse II, varicella zoster, JC virus or BK virus.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, the antibody or antigen-binding fragment as provided herein may be administered at a therapeutically effective dosage of about 0.01 mg/kg to about 100 mg/kg. In certain of these embodiments, the antibody or antigen-binding fragment is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the antibodies or antigen-binding fragments disclosed herein may be administered alone or in combination with one or more additional therapeutic means or agents. For example, the antibodies or antigen-binding fragments disclosed herein may be administered in combination with another therapeutic agent, for example, a chemotherapeutic agent or an anti-cancer drug.

In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of using the anti-TIM-3 antibodies or antigen-binding fragments thereof.

In some embodiments, the present disclosure provides methods of detecting presence or amount of TIM-3 in a sample, comprising contacting the sample with the antibody or antigen-binding fragment thereof, and determining the presence or the amount of TIM-3 in the sample.

In some embodiments, the present disclosure provides methods of diagnosing a TIM-3 related disease or condition in a subject, comprising: a) contacting a sample obtained from the subject with the antibody or antigen-binding fragment thereof provided herein; b) determining presence or amount of TIM-3 in the sample; and c) correlating the existence of the TIM-3 to the TIM-3 related disease or condition in the subject.

In some embodiments, the present disclosure provides kits comprising the antibody or antigen-binding fragment thereof provided herein, optionally conjugated with a detectable moiety. The kits may be useful in detection of TIM-3 or diagnosis of TIM-3 related disease.

In some embodiments, the present disclosure also provides use of the antibody or antigen-binding fragment thereof provided herein in the manufacture of a medicament for treating a TIM-3 related disease or condition in a subject, in the manufacture of a diagnostic reagent for diagnosing a TIM-3 related disease or condition.

Advantages

The antibodies provided herein are advantageous over existing therapies in many aspects. For example, the antibodies provided herein are better than existing TIM3 antibodies, in that the antibodies provided herein showed better in vitro efficacy in regulating T cell function in human MLR assays, specifically binding to human TIM-3 protein without cross-family reactions, and are potent to modulate immune responses.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1: Generation of Hybridoma Antibody

1. Research Materials Preparation 1.1 Antigens: DNA sequences encoding truncated (ECD and transmembrane) or full length of human TIM-3 (NM 032782.3), mouse TIM-3 (NM 134250.2) and cynomolgus monkey TIM-3 (EHH54703.1) were synthesized in Sangon Biotech (Shanghai, China), and then subcloned into modified pcDNA3.3 expression vectors with different tag (such as 6×his, AVI-6×his, human Fc, or mouse Fc) in C-terminal.

Expi293 cells were transfected with the purified expression vector. Cells were cultured for 5 days and supernatant was collected for protein purification using Ni-NTA column, Protein A column or Protein G column. The obtained human TIM-3.ECD.MBPAVIHIS, mouse TIM-3.ECD.mFc were analyzed by SDS-PAGE and SEC, and then stored at −80° C.

1.2 Benchmark (BMK) antibodies: Existing anti-TIM-3 antibodies were made as benchmark antibodies. These included: W340-BMK4 (disclosed as ABTIM3 in U.S. Pat. No. 9,605,070) and W340-BMK6 (disclosed as mAb15 in US20160200815). DNA sequences encoding the variable region of W340-BMK4 and W340-BMK6 were synthesized in Sangon Biotech (Shanghai, China), and then subcloned into modified pcDNA3.3 expression vectors with the constant region of mouse IgG1 and human IgG4 (S228P), respectively.

The plasmid containing VH and VL gene were co-transfected into Expi293 cells. Cells were cultured for 5 days and supernatant was collected for protein purification using Protein A column or Protein G column. The obtained antibodies were analyzed by SDS-PAGE and SEC, and then stored at −80° C.

1.3 Stable cell lines: Using Lipofectamine 2000, CHO-K1 or 293F cells were transfected with the expression vector containing gene encoding full length human TIM-3, mouse TIM-3 or cynomolgus monkey TIM-3. Cells were cultured in medium containing proper selection marker. Human TIM-3 high expression stable cell line (W340-CHO-K1.hPro1.G2), lower expression stable cell line (W340-CHO-K1.hPro1.H1) and mouse TIM-3 high expression stable cell line (W340-CHO-K1.mPro1.D3), cynomolgus TIM-3 high expression stable cell line (W3-293F.cynoPro1.FL-17), lower expression stable cell line (W340-293F.cynoPro1.FL-4) were selected after limited dilution.

Jurkat E6-1 cells were transfected with plasmid IL-2P Luc by SE Cell Line 4D-Nucleofector® X Kit according to the manufacturer's protocol. 48 hours after transfection, Hygromycin was added to the cell culture to select Jurkat E6-1 cells stably transfected with IL-2P Luc (Jurkat E6-1.IL-2P). The plasmid containing full length hTIM-3 was then transfected to Jurkat E6-1.IL-2P cells using the same method. 48 hours after transfection, Blasticidin S was added to the cell culture to develop the stable cell pool of Jurkat E6-1.IL-2P.hTIM-3. Stable cell lines were obtained by limited dilution.

2. Hybridoma Generation 2.1 Immunization: SD rats, 6-8 weeks of age, were immunized weekly by footpad and subcutaneous injections with 25 μg/animal of W340-hPro1.ECD.mFc or 25 μg/animal of W340-mPro1.ECD.hFc in adjuvant alternately.

2.2 Serum titer detection: Post the 4$^{th}$ immunization, serum samples were collected and examined every two weeks. Anti-hTIM-3 and anti-mTIM-3 antibody titers in the serum samples were determined by ELISA. Briefly, the plates coated with hTIM-3.ECD.His or mTIM-3.ECD.His were co-incubated with diluted rat serum (first 1:100, then 3-fold dilution in 2% BSA/PBS) for two hours. Goat anti rat-IgG-Fc-HRP was used as secondary antibody. The color was developed by dispensing 100 μL of TMB substrate, and then stopped by 100 μL of 2N HCl. The absorbance was read at 450 nM using a microplate spectrophotometer.

2.3 Hybridoma generation: When the serum antibody titer was sufficiently high, rats were given a final boost with both human and mouse TIM-3 ECD protein in D-PBS without adjuvant. On the day of fusion, lymph nodes and spleen were removed from immunized animal under sterile condition, and prepared into single cell suspension. The isolated cells were then mixed with myeloma cell SP2/0 at a ratio of 1:1. Electro cell fusion was performed using BTX 2001 Electro cell manipulator according to manufacturer's instruction. The cells were then seeded in 96-well plates at the density of $1 \times 10^4$ cells/well, and cultured at 37° C., 5% $CO_2$, until ready for screening.

2.4 Antibody screening and subcloning: human TIM-3-expressing cell binding assay by mirrorball was used as first screen method to test the binding of hybridoma supernatants to human TIM-3. Briefly, hybridoma supernatant samples, positive control and negative control were added into the 384-well plates, and co-incubated with human TIM-3 transfectant cells (W340.CHO-K1.hPro1.G2). Goat anti-rat IgG Fc PE antibody was used to determine the binding of anti-hTIM-3 antibody to the cells. Samples that had MFI≥100 were considered positive hTIM-3 binders (NC:− 15~10).

In order to confirm the initial binding results, the positive hybridoma line was further tested by FACS using W340.CHO-K1.hPro1.G2 as follow: Hybridoma supernatants were added to the cells, and the binding of rat antibodies onto the surface of the cells were detected by Alexa647-labeled goat anti-rat antibody. The MFI was evaluated by a flow cytometer and analyzed by FlowJo. Antibody binding to parental CHO-K1 cells was used as negative control.

Once specific binding was verified through first and confirmation screening, the positive hybridoma cells were subcloned to get monoclonal anti-hTIM-3 antibodies by using semi-solid medium approach. The positive clones were confirmed by binding ELISA and FACS against human TIM-3 as described above. The exhausted supernatant of selected single clones was collected for purification.

3. Hybridoma Sequencing and Antibody Humanization 3.1 Hybridoma Cell Sequencing: Total RNAs were isolated from monoclonal hybridoma cells by using RNeasy Plus Mini Kit. First strand cDNA was prepared as follows:

cDNA Amplification Reaction (20 μL)

| Component | Amount |
| --- | --- |
| Up to 5 μg total RNA | 5 μL |
| Primer (50 μM oligo(dT)$_{20}$/50 ng/μL random hexamers) | 1 μL/1 μL |
| Annealing Buffer | 1 μL |
| RNase/DNase-free water | to 8 μL |
| 65° C. for 5 min, then immediately place on ice for at least 1 minute | |
| 2X First-Strand Reaction Mix | 10 μL |
| SuperScript ™ III/RNaseOUT ™ Enzyme Mix | 2 μL | cDNA Amplification Reaction Condition

|  | Step 1 | Step 2 | Step 3 | Step 4 |
|---|---|---|---|---|
| Temperature (° C.) | 25 | 50 | 85 | 4 |
| Time | 10 min | 50 min | 5 min | ∞ |

Antibody VH and VL genes were amplified from cDNA using 3'-constant region degenerated primer and 5'-degenerated primer sets, which are complementary to the upstream signal sequence-coding region of Ig variable sequences. The PCR reaction was done as follows:
PCR Reaction System (50 μL)

| Component | Amount |
|---|---|
| cDNA | 2.0 μL |
| Premix Ex Taq | 25 μL |
| 5'- degenerated primer sets (10 pM) | 2.5 μL |
| 3'- constant region degenerated primer (10 pM) | 1 μL |
| ddH$_2$O | 19.5 μL |

PCR Reaction Condition

|  | Step 1 | Step 2 | Step 3 | Step 4 | Step 5 |
|---|---|---|---|---|---|
| Temperature (° C.) | 95 | 94 | 58 | 72 | 72 |
| Time | 4 min | 45 sec | 45 sec | 1 min | 10 min |
| Cycles | NA |  | 30 |  | NA |

PCR product (10 μL) was ligated into pMD18-T vector and 10 μL of the ligation product was transformed into Top10 competent cells. Transformed cells were plated on 2-YT+Cab plates and incubated overnight at 37° C. 15 positive clones were randomly picked for sequencing by Biosune.

3.2 Chimeric Antibody Construction (W3402-x)

The VH and VL of TIM-3 hybridoma antibody were amplified by PCR. The PCR products were purified with PCR clean-up kit. The VL and VH were sequentially cloned into pCI vector containing human IgG4 Fc. The resulting vector expressed chimeric antibody construction W3402-x comprising the variable region of W3402 and the constant region of human IgG4.

Once the sequences of inserted VL and VH were verified by sequencing, the expression vector containing the whole IgG sequence of the chimeric TIM-3 antibody was used for transient production.

3.3 Humanization

"Best Fit" approach was used to humanize the light and heavy chains of W3402. The amino acid sequences of VH and VL were blasted against in-house human germline V-gene database. The first sequences of the humanized VH and VL were derived by replacing human CDR sequences in the top hit with the W3402's CDR sequences using Kabat CDR definition. Frameworks were defined using extended CDR definition, where Kabat CDR1 was extended by 5 amino acids at the N-terminus. For heavy chains, sixteen additional sequences were created by adding back mutations based on the first humanized VH sequence.

Humanized genes were back-translated, codon-optimized for mammalian expression, synthesized by GENEWIZ, constructed into WuXi Biologics' proprietary expression vector and expressed using 293F or Expi-293F cells. The binding affinity to hTIM-3 of the humanized variant (see Table 5) was compared to that of the chimeric antibody (see Table 4) by $K_{off}$ ranking using SPR (Table 6).

Table 4 shows the full kinetic binding affinity of the parental chimeric W3402-x to human TIM-3 by SPR.

| Target | Antibody | ka (1/Ms) | kd (1/s) | KD (M) |
|---|---|---|---|---|
| hTIM-3.ECD.his | parental chimeric W3402-x | 2.26E+06 | 2.12E−05 | 9.37E−12 |

Table 5 shows the analysis of humanization score of the humanized variant W3402-z3.

| Lead antibody |  | Germline | FR1 | FR2 | FR3 | FR4 | Humanization score |
|---|---|---|---|---|---|---|---|
| W3402-z3 | zVH3 | IGHV4-59*02 | 100% | 100% | 91% | 100% | 98.88% |
|  | zVK1 | IGKV2-29*02 | 100% | 100% | 100% | 100% |  |

3.4 $K_{off}$ Ranking: the humanized variants, the parental chimeric antibody, as well as negative control were injected to the sensor chip (GLM), which was pre-coated with anti-human IgG. After the chip was washed to obtain a stable baseline, the analyte W340-hPro1.ECD.His was injected to the chips at a flow rate of 100 μL/min for an association phase of 100 s, followed by 2400 s dissociation (see Table 6).

Table 6 shows the $K_{off}$ ranking results of the humanized variant W3402-z3.

| Category | Antibody ID | kd (1/s) |
|---|---|---|
| Parental xAb | chimeric W3402-x | 1.95E−06 |
| Humanized variant | W3402-z3 | <1.00E−06 |

PTM Removal

There is a potential isomerization site "DG" located in VH-CDR3 of the W3402-z3. PTM removal was performed by introducing direct mutations at the potential PTM site. However, all PTM removed variants showed significant binding affinity loss, suggesting this site is critical for the antibody/antigen interaction.

Example 2: In Vitro Characterization

1. Full kinetic binding affinity to human TIM-3 tested by surface Plasmon resonance (SPR): W3402-z3 was injected to the sensor chip (CM5), which was pre-coated with anti-human IgG. After the chip was washed to obtain a stable baseline, various concentrations of analyte human TIM-3 and running buffer were injected to the chip at a flow rate of 30 μL/min for an association phase of 180 s, followed by 2400 s dissociation. The association and dissociation curve was fit to a 1:1 Langmiur binding model using ProteOn software (see Table 7).

Table 7 shows the full kinetic binding affinity of the humanized variant W3402-z3, to human TIM-3 by SPR, which was selected as final lead for full characterization.

| Target | Antibody | ka (1/Ms) | kd (1/s) | KD (M) |
|---|---|---|---|---|
| hTIM-3.ECD.his | W3402-z3 | 2.41E+06 | 1.01E−04 | 4.21E−11 |

2. Full kinetic binding affinity to cynomolgus monkey TIM-3 tested by surface Plasmon resonance (SPR): the sensor chip (CM5) was pre-coated with cynomolgus monkey TIM-3.ECD protein. Various concentrations of the W3402-z3 were injected over the sensor chip at a flow rate of 30 μL/min for an association phase of 200 s, followed by 2400 s dissociation. The association and dissociation curve was fit to a 1:1 kinetics mode using Biacore 8K software (Table 8).

Table 8 shows the full kinetic binding affinity of W3402-z3 to cynomolgus monkey TIM-3 by SPR.

| Target | Antibody | ka (1/Ms) | kd (1/s) | KD (M) |
|---|---|---|---|---|
| W340-cynoPro1.ECD.Fc | W3402-z3 | 5.61E+06 | 1.17E−04 | 2.09E−11 |

3. Human TIM-3 binding (FACS): various concentrations of W3402-z3, positive and negative controls were added to hTIM-3-expressing transfectant cells, and then the binding of antibodies onto the surface of the cells was detected by PE-labeled goat anti-human IgG-Fc antibody. MFI of the cells was measured by a flow cytometer and analyzed by FlowJo.

The binding of humanized W3402-z3 on human TIM-3 transfected cells is shown in FIG. 1A. The antibody can strongly bind to cell surface human TIM-3 with an $EC_{50}$ of 0.23 nM.

Figure 1B:
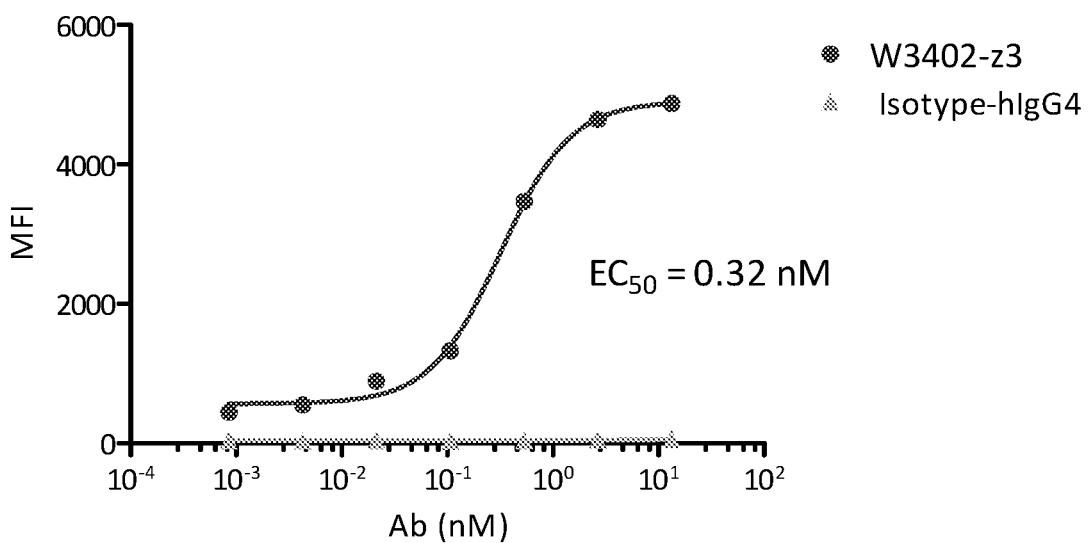

4. Cross species binding (FACS): the binding of TIM-3 antibodies to cynomolgus monkey TIM-3 was determined by FACS. Various concentrations of W3402-z3, positive and negative controls were added to cyno TIM-3-expressing transfectant cells, and then the binding of antibodies onto the surface of the cells was detected by PE-labeled goat anti-human IgG-Fc antibody. MFI of the cells was measured by a flow cytometer and analyzed by FlowJo. FIG. 1B indicates that the antibody showed strong binding to cynomolgus monkey TIM-3 with an $EC_{50}$ of 0.32 nM.

5. Resting and activated human CD4 T cells binding: It is known that TIM-3 expression can be induced on human $CD4^+$ T cells post in vitro activation (Hastings W D, et al. TIM-3 is expressed on activated human $CD4^+$ T cells and regulates Th1 and Th17 cytokines. Eur J Immunol. 2009; 39:2492-501). To determine whether W3402-z3 can bind to natural human TIM-3, freshly purified human $CD4^+$ T cells were activated to induce TIM-3 expression. Human peripheral blood mononuclear cells (PBMCs) were freshly isolated from healthy donors using Ficoll-Paque PLUS gradient centrifugation. Human $CD4^+$ T cells were isolated using Human $CD4^+$ T Cell Enrichment Kit according to the manufacturer's protocol. Purified human $CD4^+$ T cells were stimulated with PHA or left unstimulated for three days. Various concentrations of W3402-z3 as well as negative control were added to resting or activated human $CD4^+$ T cells, and then the binding of antibodies onto the surface of the human $CD4^+$ T cells was detected by PE-labeled goat anti-human IgG-Fc antibody. MFI of the cells was measured by a flow cytometer and analyzed by FlowJo.

Figure 2A:
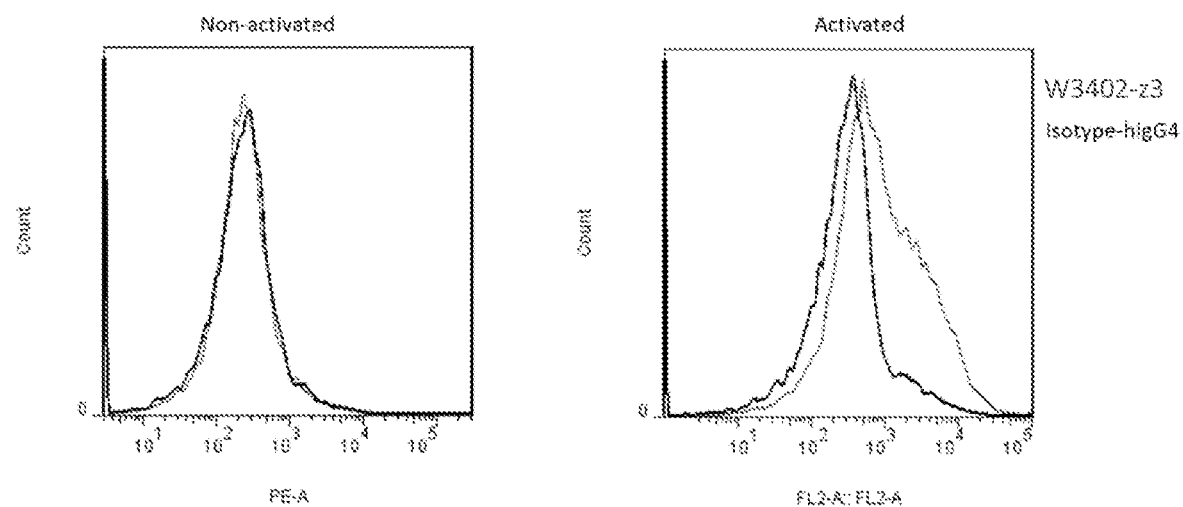
FIG. 2A shows the binding histogram of W3402-z3 on activated or non-activated CD4+ T cells. The binding curve of W3402-z3 binding on to activated CD4+ T cells is shown in FIG. 2B.
Figure 2B:
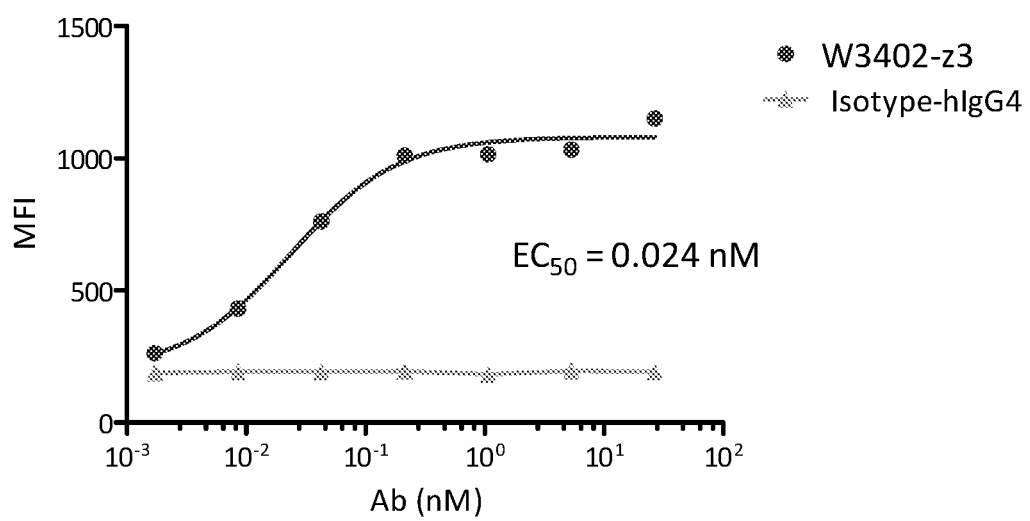
FIG. 2 shows the result of W3402-z3 binding to activated, but not resting CD4+ T cells.

As shown in FIG. 2A-2B, W3402-z3 binds to activated, but not resting $CD4^+$ T cells. FIG. 2A shows the binding histogram of W3402-z3 to activated and non-activated $CD4^+$ T cells. The binding curve of W3402-z3 to activated $CD4^+$ T cells is shown in FIG. 2B.

Figure 3A:
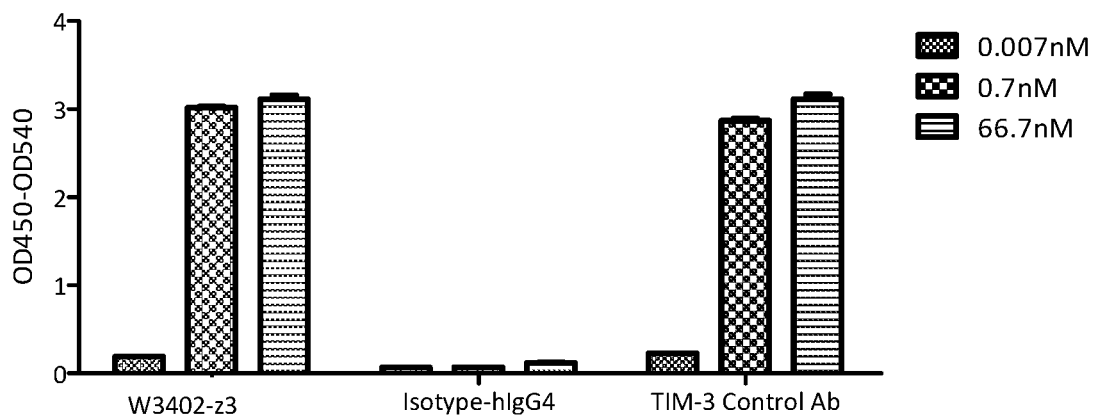
FIG. 3 shows the result of cross-family test. W3402-z3 binds specifically to human TIM-3 (FIG. 3A), with no cross-reactive binding to human TIM-1 (FIG. 3B) or TIM-4 (FIG. 3C).
Figure 3B:
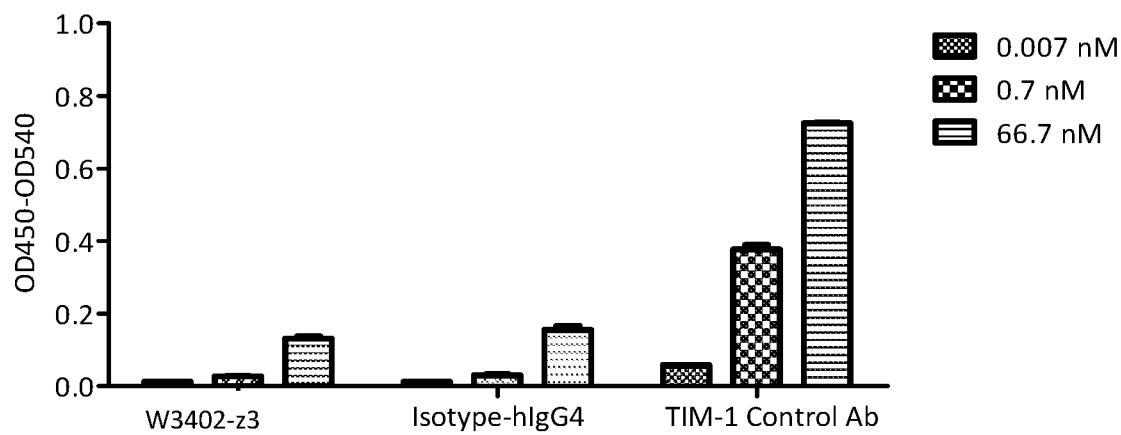
Figure 3C:
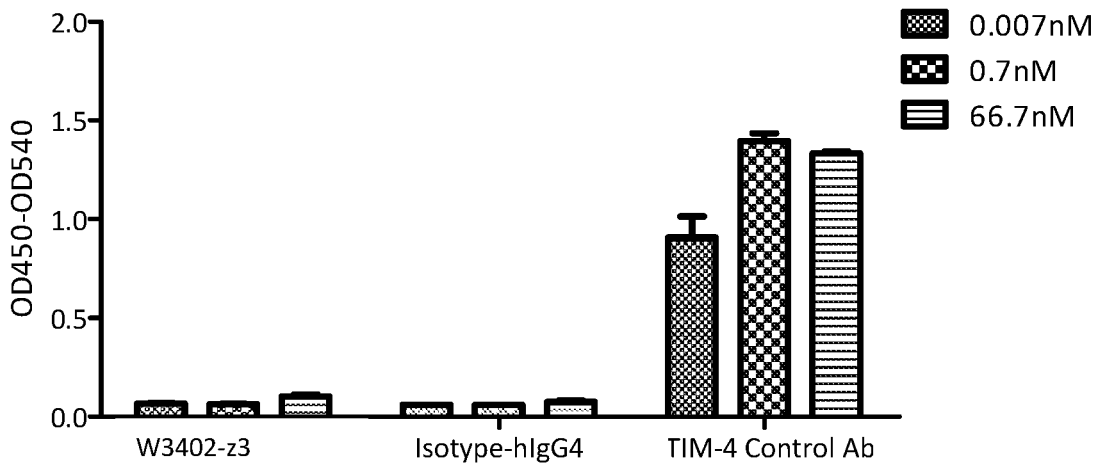

6. Paralog/Specificity (ELISA): To test whether it specifically binds to human TIM-3, but not cross-reacts to the other TIM family members, the binding of W3402-z3 to human TIM-1 and TIM-4 was determined by ELISA. W3402-z3, positive and negative control antibodies were added to the plates that were pre-coated with either human TIM-1 or TIM-4. The binding of the antibodies to the plates was detected by corresponding HRP-conjugated $2^{nd}$ antibodies (see FIGS. 3A-3C). FIG. 3 shows W3402-z3 binds specifically to human TIM-3 (FIG. 3A), with no cross-reactive binding to human TIM-1 (FIG. 3B) or TIM-4 (FIG. 3C).

Figure 4A:
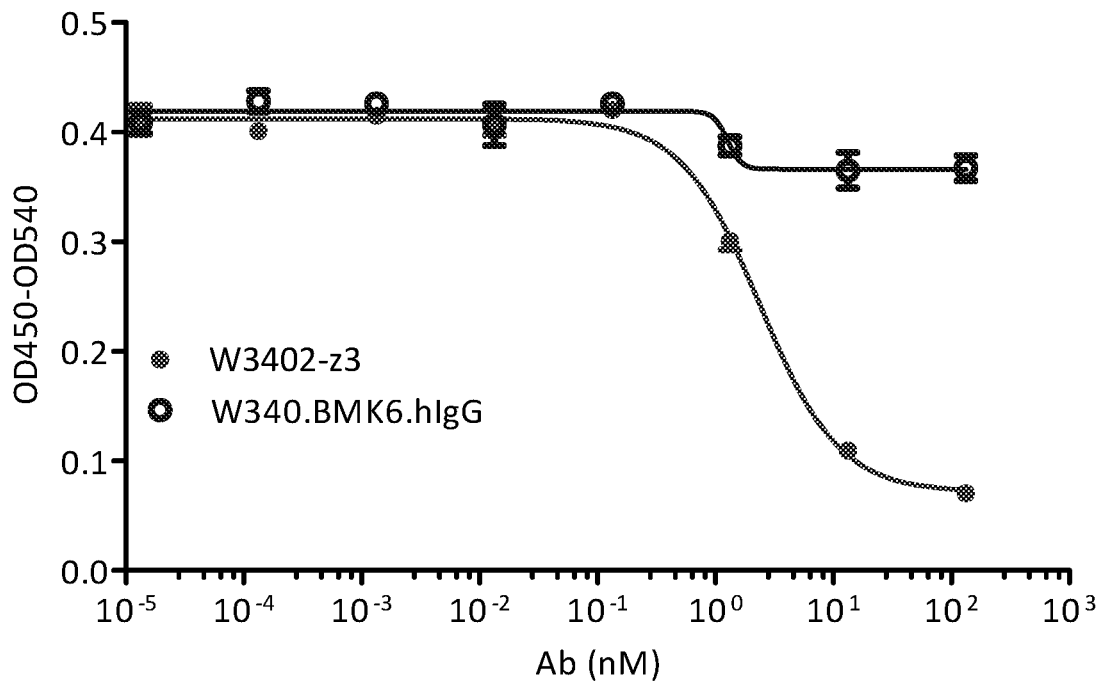
FIG. 4 shows the results of epitope binning assay suggesting that W3402-z3 is in the same or close epitope bin as benchmark W340-BMK4 (FIG. 4B); but not W340-BMK6 (FIG. 4A).
Figure 4B:
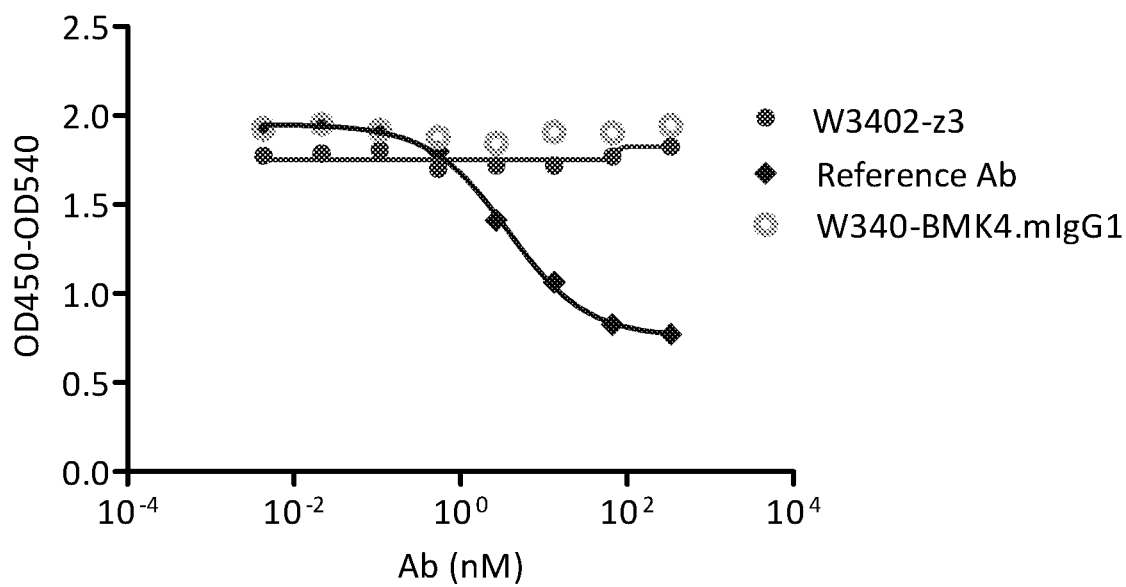

7. Epitope binning with BMK antibodies: Various concentrations of testing antibodies were mixed with certain amount of W340-BMK4.mIgG1 and W340-BMK6.hIgG, respectively. The mixtures were then added to the plates pre-coated with human TIM-3 protein. The binding of the W340-BMK4.mIgG1 and W340-BMK6.hIgG to the plates was detected by HRP-conjugated anti-mFc antibody and SA-HRP, respectively (see FIG. 4). FIGS. 4A and 4B suggest that W3402-z3 is in the same or close epitope bin as benchmark W340-BMK4 (US20150218274) (FIG. 4B); but not W340-BMK6 (US20160200815) (FIG. 4A) for binding to human TIM-3.

8. In Vitro Functionality Tests 8.1 Reporter gene assay: To test whether W3402-z3 can functionally counteract the role of TIM-3 in regulating T cell response, we transfected Jurkat cells with TIM-3 and IL-2 luciferase reporter gene. It has been implicated by Ferris et al. that TIM-3 may contribute to T cell exhaustion by enhancing TCR signaling, at least under acute conditions (Ferris R L, Lu B, Kane L P. Too much of a good thing? Tim-3 and TCR signaling in T cell exhaustion. J Immunol. 2014; 193: 1525-30). Consistent with Ferris' finding, the TIM-3 overexpressing Jurkat cells showed increased IL-2 reporter gene signal post anti-CD3/CD28 stimulation.

The $TIM-3^+$ Jurkat cells were activated by anti-CD28 antibody and anti-CD3 antibody in the presence of various concentrations of testing antibodies overnight at 37° C., 5% $CO_2$. After incubation, reconstituted luciferase substrate was added and the luciferase intensity was measured by a microplate spectrophotometer.

Figure 5:
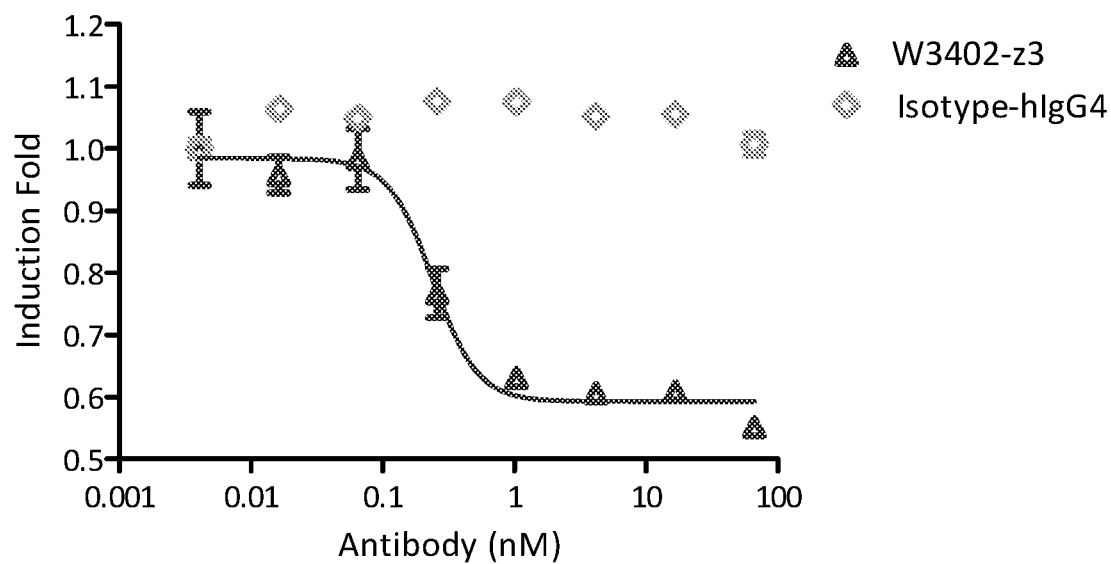
FIG. 5 shows the results of reporter gene assay indicating that W3402-z3 can counteract the effect of TIM-3 and modulate TIM-3+ Jurkat post activation.

FIG. 5 shows that W3402-z3 can counteract the effect of TIM-3 and modulate $TIM-3^+$ Jurkat post activation.

8.2 Allogeneic mixed lymphocyte reaction (MLR): PBMCs and human $CD4^+$ T cells were isolated and purified as described above. Monocytes were isolated using CD14 Micro Beads according to the manufacturer's instructions. Cells were cultured in medium containing GM-CSF and IL-4 for 5 to 7 days to generate dendritic cells (DC). Purified $CD4^+$ T cells were co-cultured with allogeneic mature DCs (mDCs) together with various concentrations of W3402-z3 in 96-well plates. On Day 5, the culture supernatants were harvested for IFNγ tests.

Figure 6:
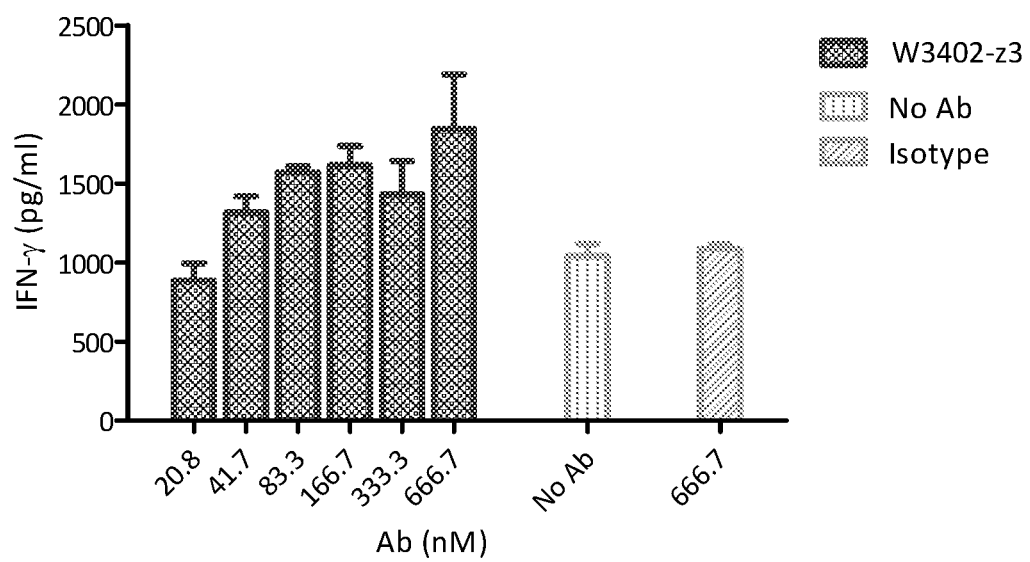
FIG. 6 shows the results of human allogeneic MLR demonstrating that W3402-z3 can enhance the IFNγ production of human CD4+ T cell in a dose dependent manner.

FIG. 6 demonstrates that W3402-z3 can enhance the IFNγ production of human $CD4^+$ T cell in a dose dependent manner.

8.3 Antigen-specific MLR: PBMCs and iDCs were obtained as described above. PBMCs were treated with CMV-pp65 and IL-2 for 5 days, and then CD4+ T cells were isolated as described above. Autologous iDCs were pulse stimulated with CMV-pp65. In the presence of autologous iDCs, purified CD4+ T cells were co-cultured with various concentrations of W3402-z3 in 96-well plates. IL-2 and IFNγ production was determined on Day 3 and Day 5, respectively. The cells were harvested at Day 5 to measure CD4+ T cell proliferation by $^3$H-thymidin incorporation assay.

Human IFNγ and IL-2 ELISA: the plates were pre-coated with capture antibody specific for human IFNγ (cat #Pierce-M700A) or IL-2 (cat #R&D-MAB602), respectively. The biotin-conjugated anti-IFNγ antibody (cat #Pierce-M701B) or anti-IL-2 antibody (cat #R&D-BAF202) was used as detecting antibody.

Proliferation assay: $^3$H-thymidine (cat #PerkinElmer-NET027001MC) was diluted 1:20 in 0.9% NaCl solution, and added to the cell culture plates at 0.5 uCi/well. The plates were cultured in 5% $CO_2$ at 37° C. for 16 to 18 hours, before the incorporation of $^3$H-thymidine into the proliferating cells was determined.

Figure 7A:
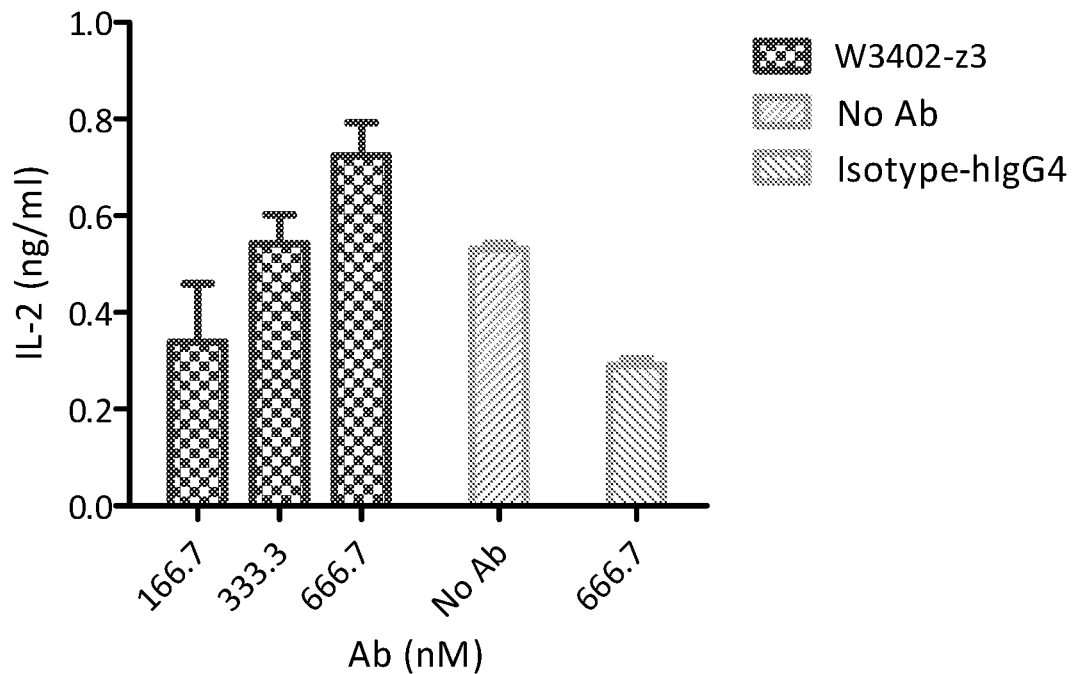
FIG. 7 shows the results of human antigen-specific MLR demonstrating that W3402-z3 can enhance the IL-2 production (FIG. 7A) of human CD4+ T cells in a dose-dependent manner, W3402-z3 can enhance the IFNγ production (FIG. 7B) as well as the proliferation (FIG. 7C) of human CD4+ T cells.
Figure 7B:
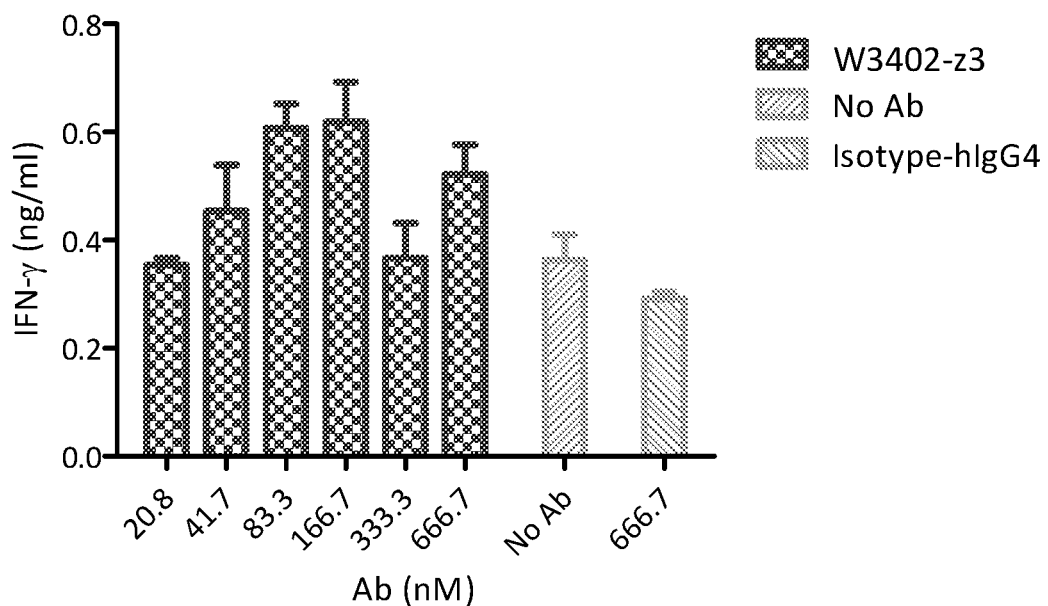
Figure 7C:
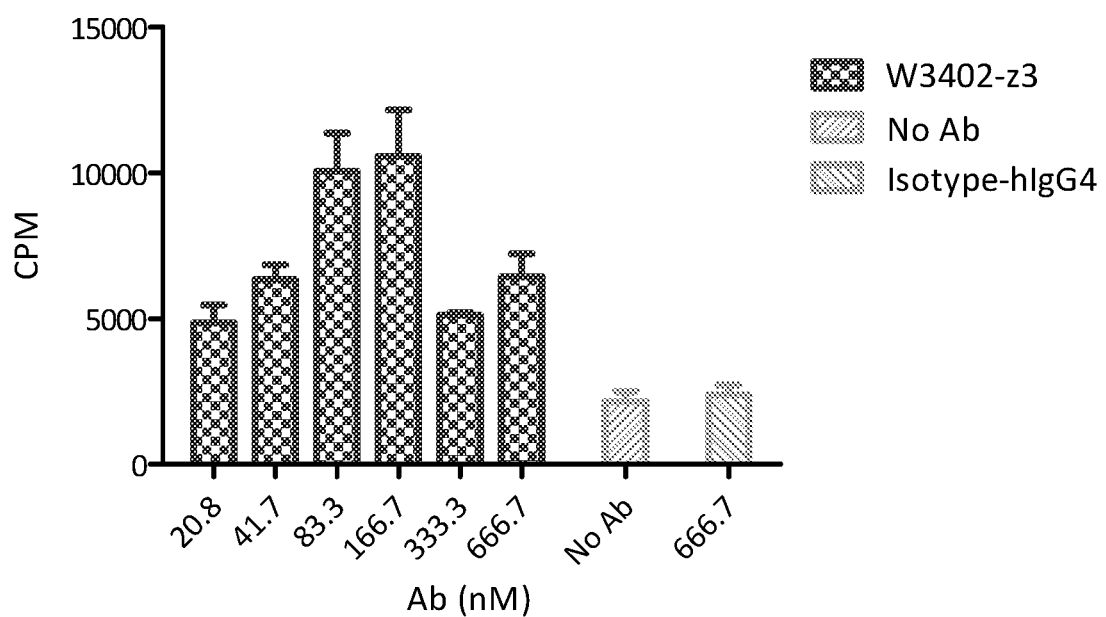

FIGS. 7A-7C demonstrate that W3402-z3 can enhance the IL-2 production (FIG. 7A) of human CD4+ T cells in a dose-dependent manner, W3402-z3 can enhance the IFNγ production (FIG. 7B) as well as the proliferation (FIG. 7C) of human CD4+ T cells.

8.4 Regulatory T cell inhibition assay: CD4+ T cells were isolated as described above. CD4+ T cells were then separated into Treg (CD4+CD25+) and CD4+CD25$^{low/-}$ T cells using Human CD4+CD25$^{high}$ T cell Isolation Kit according to the manufacturer's instructions. Allogeneic DCs, CD4+ CD25− T cells, Treg cells and TIM-3 antibodies were incubated in 96-well plates. The plates were kept at 37° C. in a 5% $CO_2$ incubator for 5 days. CD4+CD25− cell proliferation was determined on Day 5 by $^3$H-thymidine incorporation assay.

Figure 8A:
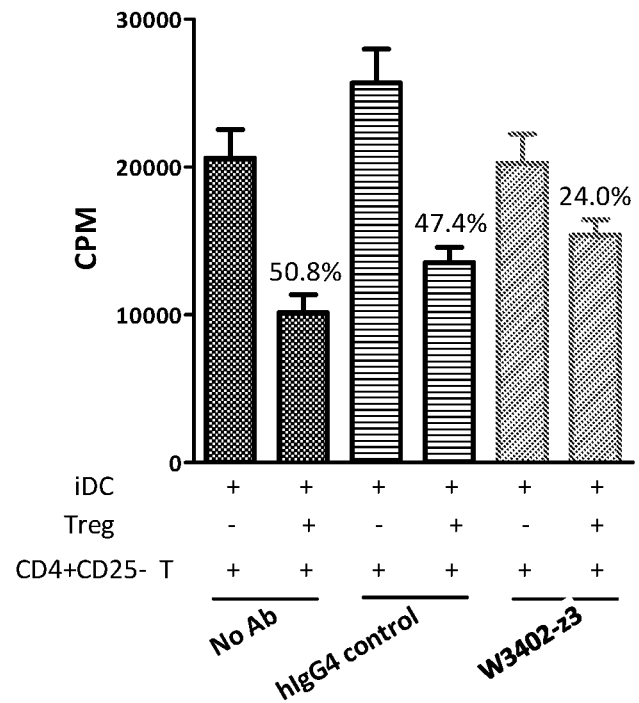
FIG. 8A shows the CD4+ T cell proliferation in the presence of W3402-z3 alone or with Treg cells.
Figure 8B:
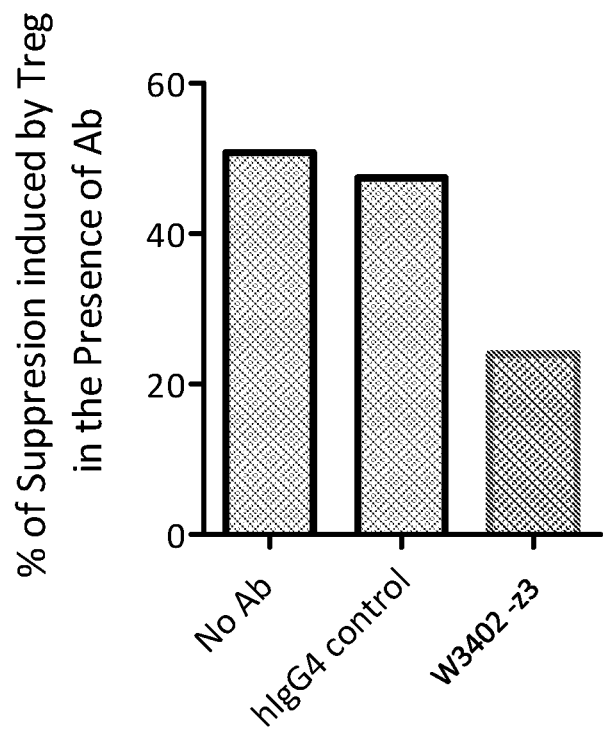
FIG. 8B shows the percentage of inhibitory effect mediated by Treg in the presence of W3402-z3 or isotype control.

FIGS. 8A and 8B demonstrate that W3402-z3 can partially block the suppressive function of Tregs in regulating CD4 T cell proliferation. FIG. 8A shows the CD4 T cell proliferation in the presence of W3402-z3 alone or with Treg cells. FIG. 8B shows the percentage of inhibitory effect mediated by Treg in the presence of W3402-z3 or isotype control.

9. Antibody-dependent cell-mediated cytotoxicity (ADCC): Human CD4+ T cells were activated to induce TIM-3 expression as described above. Activated human CD4+ T cells and various concentrations of testing antibodies were pre-incubated in 96-well plate for 30 minutes, and then PBMCs were added at the effector/target ratio of 50:1. The plate was kept at 37° C. in a 5% $CO_2$ incubator for 4-6 hours. Target cell lysis was determined by LDH-based cytotoxicity detection kit. Herceptin® induced ADCC effect on BT474 cells was used as positive control.

Figure 9:
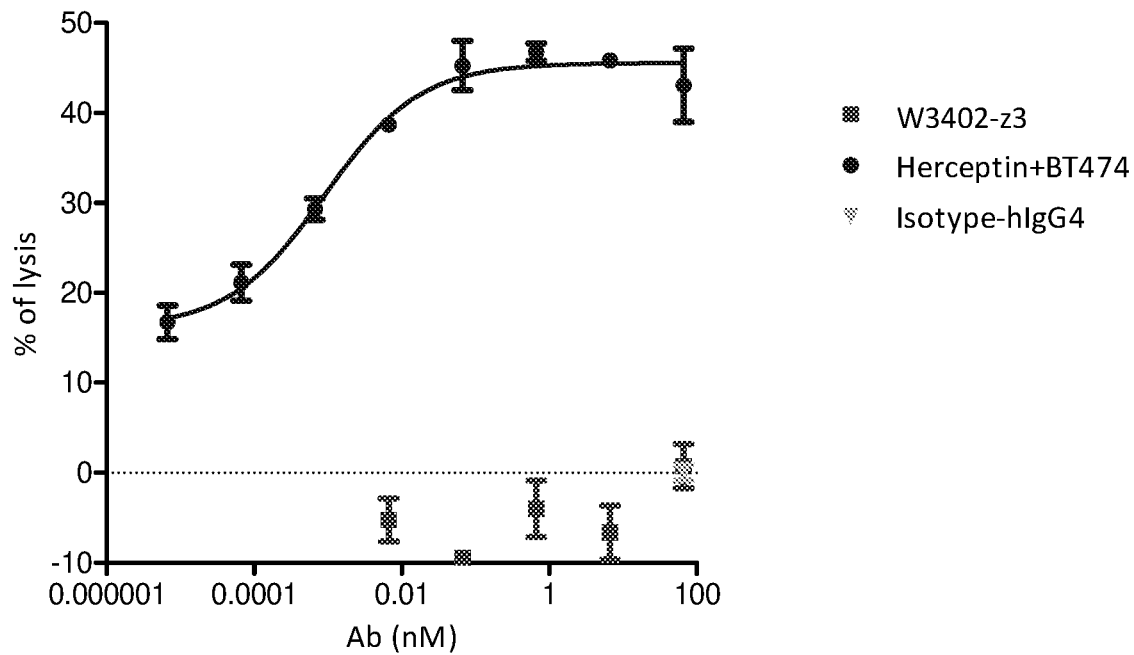
FIG. 9 shows the result of ADCC test demonstrating W3402-z3 does not mediate ADCC activity on activated CD4+ T cells. Herceptin-induced BT474 cell lysis was used as positive control for the assay system.

FIG. 9 shows the result of ADCC test demonstrating W3402-z3 does not mediate ADCC activity on activated CD4+ T cells, which can avoid the potential damage to TIM-3 positive cells while it is used to treat patients.

The IgG1 formats of W3402-z3 (in which the human IgG1 constant region contains amino acid substitution of L234F, L235E and P331S, or having an Arg inserted after position 236 along with L328R) are also tested for ADCC and CDC activities. The IgG1 formats of W3402-z3 show binding activities and blocking activities to TIM-3 at a level comparable or similar to IgG4 format of W3402-z3, and do not mediate ADCC or CDC activity on activated CD4+ T cells either (data not shown).

10. Complement dependent cytotoxicity (CDC): human activated CD4+ T cells and various concentrations of testing antibodies were mixed in 96-well plates. Human complement was added at the dilution of 1:50. The plates were kept at 37° C. in a 5% $CO_2$ incubator for 2-3 hours. Target cell lysis was determined by CellTiter-Glo. Rituxan®-induced Raji cell lysis was used as positive control.

Figure 10:
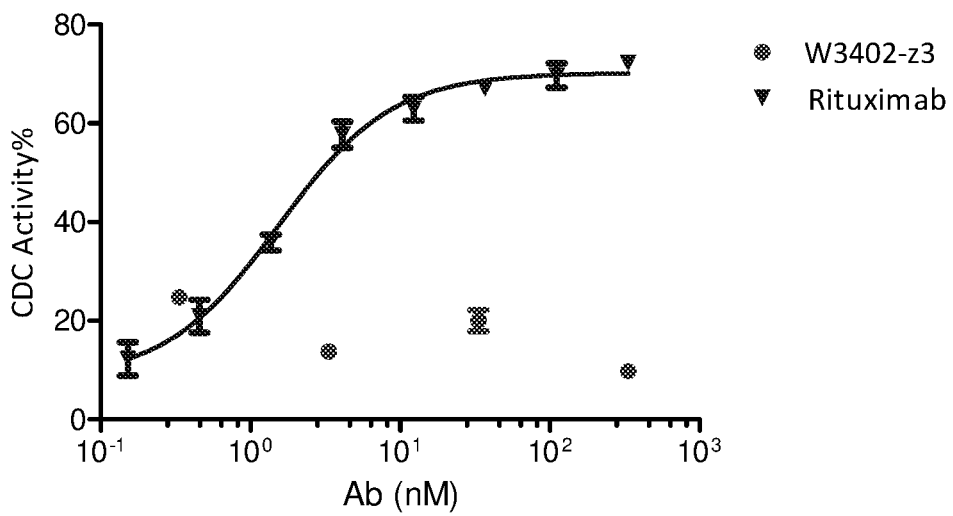
FIG. 10 shows the result of CDC test demonstrating W3402-z3 does not mediate CDC activity on activated CD4+ T cells. Rittman-induced Raji cell lysis was used as positive control for the assay system.

FIG. 10 shows the result of CDC test demonstrating W3402-z3 does not mediate CDC activity on activated CD4+ T cells.

11. Serum stability test: W3402-z3 was 1:50 diluted in freshly collected human serum, aliquoted and cultured at 37° C. in a 5% $CO_2$ incubator. At indicated time point, an aliquot of W3402-z3 was removed from culture, snap frozen, and then kept at −20° C., until ready for binding titration test by FACS as described above.

Figure 11:
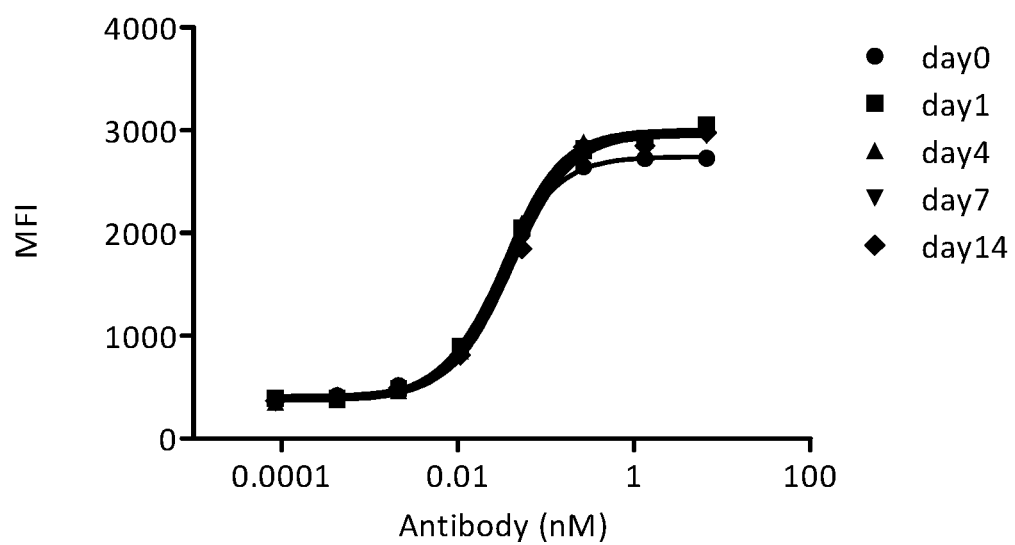
FIG. 11 suggests that the W3402-z3 is stable in human serum at 37° C. for at least 14 days.

FIG. 11 shows that the W3402-z3 is stable in human serum at 37° C. for at least 14 days.

Figure 12:
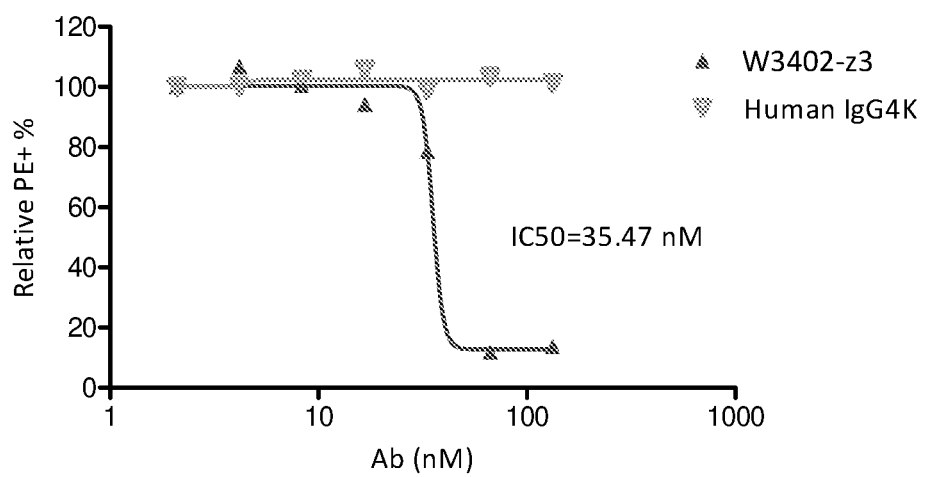
FIG. 12 shows that W3402-z3 demonstrates a dose-dependent blockade of PtdSer-TIM-3 interaction with an $IC_{50}$ of 35.47 nM.

12. PtdSer (Phosphatidylserine) Competition Assay:

It has been suggested by Sabatos-Peyton et al. (Sabatos-Peyton C A, et al. Blockade of Tim-3 binding to phosphatidylserine and CEACAM1 is a shared feature of anti-Tim-3 antibodies that have functional efficacy. Oncoimmunology. 2017; 7: e1385690) that blockade of PtdSer is a shared property of anti-TIM-3 antibodies with demonstrated functional efficacy. To determine whether W3402-z3 can block the binding between human TIM-3 and PtdSer, Jurkat E6-1 cells were treated with Paclitaxel for 2 days to induce apoptosis. Various concentrations of W3402-z3, positive and negative controls were pre-mixed with mFc-tagged human TIM-3, and then added to apoptotic Jurkat cells. The binding of human TIM-3 onto the surface of the apoptotic Jurkat cells was detected by PE-labeled anti-mouse IgG Fc antibodies. As shown in FIG. 12, W3402-z3 demonstrates a dose-dependent blockade of PtdSer-TIM-3 interaction with an $IC_{50}$ of 35.47 nM.

13. Human TIM-3 surface down-regulation (FACS): As reported by Waight J. et al, functional anti-TIM-3 antibody can induce rapid TIM-3 internalization as one of the possible mechanism of action to block the signaling of TIM-3 (Waight J, et al. INCAGN02390, a novel antagonist antibody that targets the co-inhibitory receptor TIM-3. Abstract 3825, AACR Annual Meeting 2018; Apr. 14-18, 2018; Chicago, IL). To determine whether W3402-z3 can induce cell surface hTIM-3 down-regulation, hTIM-3-expressing cells were cultured with W3402-z3 or isotype control antibody. Various concentrations of testing antibodies were added to human TIM-3-expressing transfectant cells, and cultured at 37° C., 5% $CO_2$. At the different time points, cells were harvested; and the presence of hTIM-3 on the surface of the cells was detected by biotin labeled polyclonal TIM-3 antibody followed by PE labeled SA. MFI of the cells was measured by a flow cytometer and analyzed by FlowJo.

Figure 13:
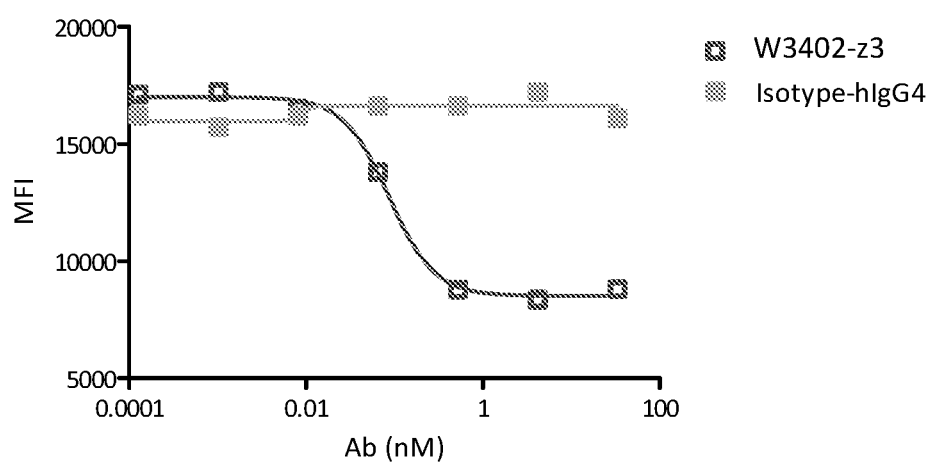
FIG. 13 shows that remarkable dose-dependent hTIM-3 down-regulation from the surface was detected as early as 4 hours post addition of the W3402-z3 into the cell culture.

As early as 4 hours post the addition of W3402-z3 into the cell culture, remarkable dose-dependent hTIM-3 down-regulation was detected (FIG. 13). It is known that internalization can be blocked by hypertonic sucrose (Hansen S H, Sandvig K, van Deurs B. Clathrin and HA2 adaptors: effects of potassium depletion, hypertonic medium, and cytosol acidification. J Cell Biol. 1993; 121(1):61-72). The down-regulation of TIM-3 was completely abolished by culturing in the hypertonic medium (complete RPMI 1640 supplemented with 1M sucrose), suggesting the W3402-z3-induced hTIM-3 down-regulation was mediated by internalization, but not shedding (data not shown).

14. Stress test: Since W3402-z3 contains a potential isomerization PTM site in its VH-CDR3 region, a stress test was performed to evaluate whether the binding affinity of the antibody was effected under the stressed condition for isomerization.

A stressed sample of W3402-z3 was prepared by buffer exchanging W3402-z3 into 20 mM Tris, 150 mM NaCl, pH 8.5 buffer using microcentrifuge desalting column (7K MWCO, Thermo Fisher) and further concentrating to 1 mg/ml using Amicon ultrafiltration filter (30K MWCO, Merck Millipore). The antibody was then incubated at 37° C. for 5 days, to provide the stressed sample of W3402-z3 (W3402-z3-stress). Binding affinities of the stressed antibody and non-stressed antibody to human TIM-3 was measured by SPR as described above.

Table 9 shows that the stressed sample (W3402-z3-stress) had comparable binding affinity to human TIM-3 to that of the non-stressed sample, indicating that the activity of W3402-z3 was not affected by the stress conditions.

| Target | Antibody | ka (1/Ms) | kd (1/s) | KD (M) |
|---|---|---|---|---|
| hTIM-3.ECD.his | W3402-z3 | 1.07E+06 | 1.04E−04 | 9.73E−11 |
| | W3402-z3-stress | 1.08E+06 | 1.02E−04 | 9.49E−11 |

---

What is claimed is:

1. An anti-TIM-3 antibody or antigen-binding fragment thereof, comprising:
a heavy chain variable region CDR1 comprising the amino acid sequence of SEQ ID NO:1, a heavy chain variable region CDR2 comprising the amino acid sequence of SEQ ID NO: 3, a heavy chain variable region CDR3 comprising the amino acid sequence of SEQ ID NO: 5,
a light chain variable region CDR1 comprising the amino acid sequence of SEQ ID NO: 2, a light chain CDR2 variable region comprising the amino acid sequence of SEQ ID NO: 4, and a light chain variable region CDR3 comprising the amino acid sequence of SEQ ID NO: 6.

2. The antibody or antigen-binding fragment thereof of claim 1, comprising a heavy chain variable region selected from the group consisting of SEQ ID NO: 7, SEQ ID NO: 11, and a homologous sequence thereof having at least 80% sequence identity to SEQ ID NO: 7 or SEQ ID NO: 11, yet retaining specific binding affinity to TIM-3; and/or comprising a light chain variable region selected from the group consisting of SEQ ID NO: 9, SEQ ID NO: 13, and a homologous sequence thereof having at least 80% sequence identity to SEQ ID NO: 9 or SEQ ID NO: 13, yet retaining specific binding affinity to TIM-3.

3. The antibody or antigen-binding fragment thereof of claim 1, comprising a heavy chain variable region comprising SEQ ID NO: 7 and a light chain variable region comprising SEQ ID NO: 9.

4. The antibody or antigen-binding fragment thereof of claim 1, comprising a heavy chain variable region comprising SEQ ID NO: 11 and a light chain variable region comprising SEQ ID NO: 13.

5. The antibody or antigen-binding fragment thereof of claim 1, further comprising an immunoglobulin constant region.

6. The antibody or antigen-binding fragment thereof of claim 1, further comprising a human IgG4 constant region or a human IgG1 constant region.

7. The antibody or antigen-binding fragment thereof of claim 1, wherein the antibody or antigen-binding fragment thereof is a humanized antibody, a single domain antibody, a diabody, a scFv, a scFv dimer, a BsFv, a dsFv, a (dsFv)$_2$, a Fv fragment, a Fab, a Fab', a F(ab')$_2$, a ds diabody, a nanobody, a scFv-Fc antibody, or a bivalent antibody.

8. The antibody or antigen-binding fragment thereof of claim 1, wherein the antibody or antigen-binding fragment thereof is capable of specifically binding to human TIM-3 at a K$_D$ value of no more than 5×10$^{-9}$M as measured by surface plasmon resonance, and/or wherein the antibody or antigen-binding fragment thereof is capable of specifically binding to human TIM-3 expressed on a cell surface at an EC$_{50}$ of no more than 5 nM as measured by flow cytometry.

9. The antibody or antigen-binding fragment thereof of claim 1, wherein the antibody or antigen-binding fragment thereof is capable of specifically binding to cynomolgus monkey TIM-3.

10. The antibody or antigen-binding fragment thereof of claim 1, wherein the antibody or antigen-binding fragment thereof is linked to one or more conjugate moieties, wherein the one or more conjugate moieties comprise a clearance-modifying agent, a toxin, a detectable label, a chemotherapeutic agent, or a purification moiety.

11. A pharmaceutical composition comprising the antibody or antigen-binding fragment thereof of claim 1, and a pharmaceutically acceptable carrier.

12. A polynucleotide encoding the anti-TIM-3 antibody or antigen-binding fragment thereof of claim 1.

13. A vector comprising the polynucleotide of claim 12.

14. A host cell comprising the vector of claim 13.

15. A method of expressing an antibody or antigen-binding fragment thereof, comprising culturing the host cell of claim 14.

16. A method of inhibiting TIM-3 signaling pathway activity in a TIM-3-expressing cell, comprising exposing the TIM-3-expressing cell to the antibody or antigen-binding fragment thereof of claim 1.

17. A method of detecting the presence or the amount of TIM-3 in a sample, comprising: a) contacting the sample with the antibody or antigen-binding fragment thereof of claim 1; and b) determining the presence or the amount of TIM-3 in the sample.

18. A kit comprising the antibody or antigen-binding fragment thereof of claim 1.

19. An antibody or antigen-binding fragment thereof that binds to TIM-3, comprising a heavy chain variable region (VH) comprising VH CDR1, VH CDR2, and VH CDR3 that are identical to VH CDR1, VH CDR2, and VH CDR3 present in SEQ ID NO: 7 or 11; and a light chain variable region (VL) comprising VL CDR1, VL CDR2, and VL CDR3 that are identical to VL CDR1, VL CDR2, and VL CDR3 present in SEQ ID NO: 9 or 13.

20. The antibody or antigen-binding fragment thereof of claim 6, wherein the human IgG4 constant region comprises the amino acid substitution S228P.

21. The antibody or antigen-binding fragment thereof of claim 6, wherein the human IgG1 constant region (1) comprises one or more amino acid substitutions selected from L234F, L235E and P331S; or (2) comprises the amino acid substitution L328R and an arginine inserted after position 236.

22. A method of treating cancer in a subject, comprising administering to the subject in need thereof a therapeutically effective amount of the antibody or antigen-binding fragment thereof of claim 1.

23. The method of claim 22, further comprising administering an anti-PD-1 antibody to the subject.

\* \* \* \* \*